United States Patent [19]

Ohto et al.

[11] Patent Number: 5,338,857
[45] Date of Patent: Aug. 16, 1994

[54] AMINOKETONE DERIVATIVES OF 1,2-OXAZOLE AND USE THEREOF

[75] Inventors: Norio Ohto; Kazutoshi Horikomi, both of Chiba; Akira Matsubara, Kanagawa; Hideki Tanada, Chiba; Kazuya Sakai, Chiba; Seitaro Kajiya, Chiba; Akira Mizuchi, Chiba; Hideshi Shimizu, Kanagawa, all of Japan

[73] Assignee: Mitsui Toatsu Chemicals Incorporated, Tokyo, Japan

[21] Appl. No.: 839,434

[22] Filed: Feb. 24, 1992

Related U.S. Application Data

[63] Continuation-in-part of Ser. No. 558,869, Jul. 30, 1990, abandoned.

[30] Foreign Application Priority Data

Aug. 4, 1989 [JP] Japan .................. 1-201410
Feb. 26, 1991 [JP] Japan .................. 3-030739

[51] Int. Cl.$^5$ .................. C07D 413/06; A61K 31/42
[52] U.S. Cl. .................. 548/248; 540/3; 540/207
[58] Field of Search ............. 540/603; 548/207, 248; 514/404, 326, 212

[56] References Cited

FOREIGN PATENT DOCUMENTS

| | | |
|---|---|---|
| 0094833 | 5/1983 | European Pat. Off. . |
| 0163537 | 5/1985 | European Pat. Off. . |
| 0273375 | 12/1987 | European Pat. Off. . |
| 0299349 | 6/1988 | European Pat. Off. . |
| 0266577A1 | 11/1988 | European Pat. Off. . |
| 0335723 | 3/1989 | European Pat. Off. . |
| 0414391A2 | 2/1991 | European Pat. Off. . |
| 1098062 | 1/1968 | United Kingdom . |
| 2107710A | 5/1983 | United Kingdom . |

OTHER PUBLICATIONS

European Search Report of 9230 1510 (European equivalent).
"The Merck Index", 11th Edition, 1989, p. 262, edited by S. Budavari et al. Merck & Co., Inc. Rahway, US.
Journal of Organic Chemistry, vol. 52, No. 25, Dec. 11, 1987, pp. 5501–5505 US; R. R. Sauers et al., "Synthesis and Photochemistry of Heterocyclic Norbornenyl Ketones", p. 5504.
Chemical Abstracts, vol. 102, No. 11, Mar. 18, 1985, p. 574, Abstract No. 95628x, Columbus, Ohio, US; JP–A–59181267 (Nippon Kayaku Co., Ltd.).
Chemical and Pharmaceutical Bulletin, vol. 34, No. 4, 1986, pp. 1643–1655; T. Tatee et al.: "Isoxazole Derivatives as Centrally Acting Muscle Relaxants II. Synthesis and Structure–Activity Relationship of 3–Amino–N–(-3–phenyl–5–isoxazolyl) propanamides", p. 1646.

*Primary Examiner*—David B. Springer
*Attorney, Agent, or Firm*—Nixon & Vanderhye

[57] ABSTRACT

Aminoketone derivative compounds containing a heterocyclic ring bonded to an aminoketone moiety and useful as effective ingredients of centrally acting muscle relaxants and pollakiurea curing agents.

(+)3-phenyl-5-[2-(1-pyrrolidinylmethyl)butyryl]isoxazole, which has a more remarkable central muscle relaxant action as compared with its racemic modification, can be effectively separated from the racemic modification using optically active 10-camphorsulfonic acid as the agent for the optical resolution.

7 Claims, No Drawings

AMINOKETONE DERIVATIVES OF 1,2-OXAZOLE AND USE THEREOF

This is a continuation-in-part of application Ser. No. 07/558,869, filed Jul. 30, 1990, now abandoned.

BACKGROUND OF THE INVENTION

1. Field of the Invention

The present invention relates to aminoketone derivatives and physiologically-acceptable salts thereof, which have muscle relaxant effects, and therapeutic agents containing them as effective ingredients. The aminoketone derivatives and the physiologically-acceptable salts thereof are useful as effective ingredients of centrally acting muscle relaxants employed for the treatment of diseases featuring spastic paralysis as a principal symptom, dolorous muscle spasticity caused by motor organ diseases, and the like; and as effective ingredients for the improvement of pollakiurea caused by neurogenic bladders or unstable bladders.

The present invention relates to optically active 3-phenyl-5-[2-(1-pyrrolidinylmethyl)butyryl]isoxazole having a centrally acting muscle relaxant action and a method for preparing the same.

2. Description of the Related Art

Some aminoketone derivatives having centrally acting muscle relaxant effects have been known to date, including tolperisone hydrochloride and eperisone hydrochloride, both clinically used these days and in addition, the compounds disclosed for example in Japanese Patent Application Laid-Open No. 39816/1988 and European Patent Publication No. 163537. Similarly to tolperisone hydrochloride and eperisone hydrochloride, the compounds disclosed in these publications all have an aromatic hydrocarbon moiety bonded to an aminoketone moiety. Further, European Patent Publication No, 273375 discloses to the effect that aminoketone derivatives having a similar structure are effective for the improvement of pollakiurea.

Tolperisone hydrochloride and eperisone hydrochloride referred to above are however not fully satisfactory as centrally acting muscle relaxants from the standpoints of strength of action, prolonged action and freedom from side effects (central depressant effects), although they are widely used for diseases featuring spastic paralysis as a principal symptom.

Heretofore, with regard to the optical resolution process of a compound having a centrally acting muscle relaxant action, techniques using an optical resolving agent are known. For example, Japanese Patent Application Laid-open No. 40779/1978 discloses a technique which comprises converting dl-tolperisone into two kinds of diastereomer salts by the use of optically active acetylphenylglycine as the resolving agent, separating these diastereomer salts mutually by the utilization of a difference of solubility thereof, and then recovering optically active tolperisone. In addition, Japanese Patent Application Laid-open Nos. 225367/1988 and 131171/1989 disclose a technique which comprises separating dl-2-methyl-1-(4-trifluoromethylphenyl)-3-pyrrolidino-1-propane by the use of optically active acetylphenylglycine or optically active malic acid as the resolving agent, and then isolating optically active 2-methyl-1-(4-trifluoromethylphenyl)-3-pyrrolidino-1-propane.

SUMMARY OF THE INVENTION

An object of the present invention is to provide an aminoketone derivative or a physiologically acceptable salt thereof, which is satisfactory in all aspects including the strength of action, prolonged action and low side effects and is hence useful as an effective ingredient of a centrally acting muscle relaxant or a pollakiurea curing agent.

Another object of the present invention is to provide both a centrally acting muscle relaxant and a pollakiurea curing agent satisfactory in all aspects including strength of action, prolonged action and low side effects.

A further object of the present invention is to provide a method for the treatment of diseases featuring spastic paralysis as a principal symptom, dolorous muscle spasticity caused by motor organ diseases, and the like.

A still further object of the present invention is to provide a method for the improvement of pollakiurea caused by neurogenic bladders or unstable bladders.

These objects can be achieved by an aminoketone derivative represented by a formula (I) to be defined herein.

Novel aminoketone derivatives and physiologically-acceptable salts thereof, to which the present invention is directed, have excellent muscle relaxation action, spinal reflex depressing action, antitremorine action, antiepileptic action and the like, and are therefore extremely useful as therapeutic agents for muscle tone caused by diseases such as dorsalgia, lumbago, disk herniation and the cervico-omobrachial syndrome and spastic paralysis caused by cerebrovascular diseases, spastic spinal paralysis and cerebral palsy. In addition, they have micturition reflex depressing action so that they are also useful as pollakiurea curing agents.

Further investigation has been continued, and as a result, it has been discovered that (+)-3-phenyl-5-[2-(1-pyrrolidinylmethyl)butyryl]isoxazole has a more remarkable central muscle relaxant action as compared with a racemic modification. However, a conventional technique cannot efficiently and optically resolve 3-phenyl--5[2-(1-pyrrolidinylmethyl)-butyryl]isoxazole.

An object of the present invention is to provide a (+) form of 3-phenyl-5-[2-(1-pyrrolidinylmethyl)butyryl]isoxazole by efficient optical resolution, and another object of the present invention is to provide an excellent central muscle relaxant.

In order to solve the above-mentioned problems, the present inventors have found that an optically active sulfonic acid, particularly optically active 10-camphorsulfonic acid is extremely effective as the resolving agent, and the present invention has been completed on the basis of this knowledge.

DETAILED DESCRIPTION OF THE INVENTION AND PREFERRED EMBODIMENTS

The aminoketone derivatives according to the present invention are compounds represented by the following

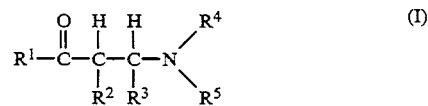

In the formula (I), R¹ represents

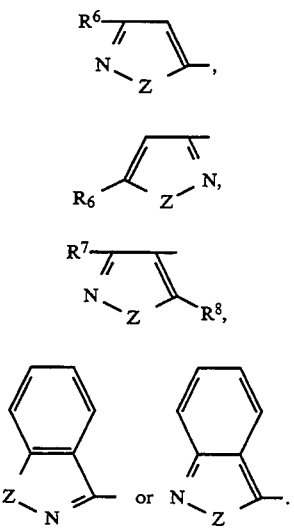

R⁶ is a halogen atom; a lower alkyl group; a benzyl group; a benzoyl group; a pyridyl group; a furyl group optionally substituted by one or more lower alkyl groups; a thienyl group optionally substituted by one or more lower alkyl groups; a phenyl group optionally substituted by one or more halogen atoms and/or one or more lower alkoxy, lower alkyl, trifluoromethyl, cyano, nitro, amino, dimethylamino, acetamido, methanesulfonylamido, acetyl and/or lower alkoxycarbonyl groups; or a naphthyl group. R⁷ and R⁸ are independently phenyl or lower alkyl groups. Z is an oxygen or sulfur atom.

R² represents a hydrogen atom, a lower alkyl, benzyl, methoxy, phenyl, allyl, trifluoromethyl- or lower-alkoxy-substituted lower alkyl, or cyclopropylmethyl group. R³ is a hydrogen atom or a lower alkyl group, or R² and R³ are coupled together to form a five- or six-membered alicyclic group.

R⁴ and R⁵ independently represent saturated or unsaturated lower alkyl groups, or R⁴ and R⁵ are coupled together into a sort of cyclic form to form at least one cyclic structure selected from the group consisting of the pyrrolidine, piperidine, hexamethyleneimine, morpholine and piperazine structures. The cyclic structure may optionally be substituted by one or more methyl, acetyl and benzyl groups.

Preferred are $C_{1-2}$ alkyl groups for the lower alkyl groups as R⁷ and R⁸, a $C_{1-3}$ alkyl group for the lower alkyl group as R⁶, $C_{1-3}$ alkyl groups for the alkyl groups substituted on the furyl and thienyl groups as R⁶, a $C_{1-2}$ alkyl group for the lower alkyl group substituted on the phenyl group as R⁶, a $C_{1-2}$ alkoxy group for the alkoxy group substituted on the phenyl group as R⁶, a $C_{1-2}$ alkyl group for the lower alkyl group substituted on the phenyl group as R⁶, a $C_{1-2}$ alkoxy group for the lower alkoxy group substituted on the phenyl group as R⁶ and a $C_{1-2}$ alkoxy group for the alkoxy group of the lower alkoxycarbonyl group substituted on the phenyl group as R⁶. Also preferred are a $C_{1-4}$ alkyl group for the lower alkyl group as R² and a $C_{1-2}$-alkoxy-substituted $C_{1-2}$ lower alkyl group for the lower-alkoxy-substituted lower alkyl group as R². A $C_{1-2}$ alkyl group is preferred for the lower alkyl group as R³. Furthermore, $C_{1-4}$ saturated or unsaturated alkyl groups are preferred for the saturated or unsaturated lower alkyl groups as R⁴ and R⁵.

Illustrative of the unsaturated lower alkyl groups as R⁴ and R⁵ include lower alkyl groups containing one double bond, for example, 2-propenyl group and 2-butenyl group.

The aminoketone derivatives represented by the formula (I) and physiologically-acceptable salts thereof, to which the present invention is directed, have excellent centrally acting muscle relaxation action and high safety, and are therefore extremely useful as effective ingredients of centrally acting muscle relaxants.

The aminoketone derivatives represented by the formula (I) includes various optical isomers as they have an asymmetric carbon atom. It is to be noted that these isomers are all embraced by the present invention.

Exemplary physiologically-acceptable acid addition salts of the aminoketone derivatives of the invention include inorganic acid salts formed with hydrochloric acid, sulfuric acid, phosphoric acid and the like; and organic acid salts formed with acetic acid, citric acid, succinic acid, maleic acid, fumaric acid, tartaric acid, methanesulfonic acid, lactic acid and the like.

The aminoketone derivatives of the invention can be obtained, for example, by processes including the following preparation route A or B or by the processes described in examples to be given subsequently. Preparation Route A:

Preparation Route A:

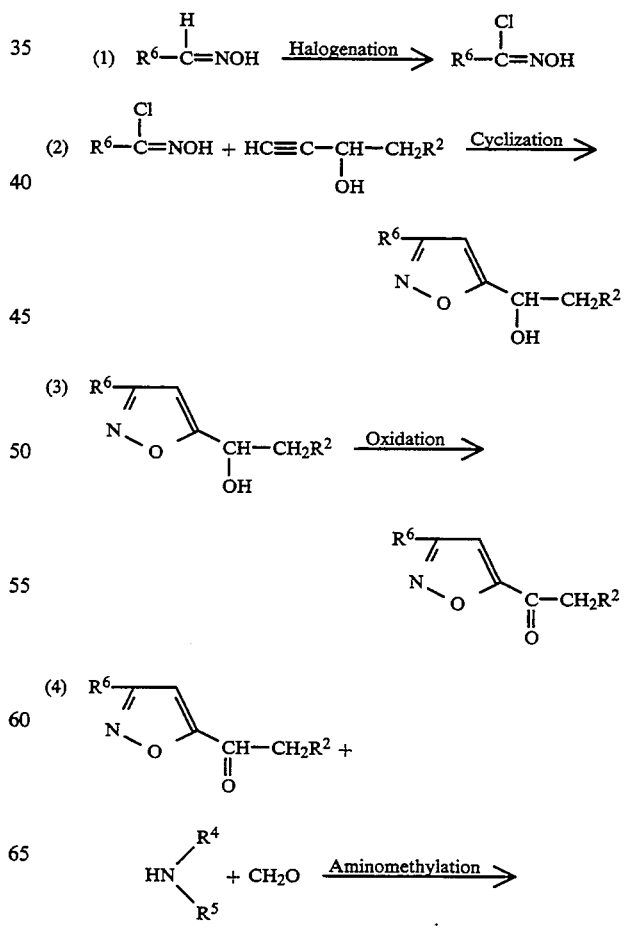

-continued

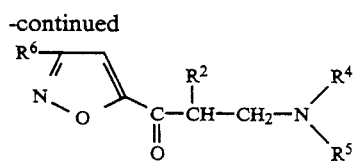

Preparation Route B:

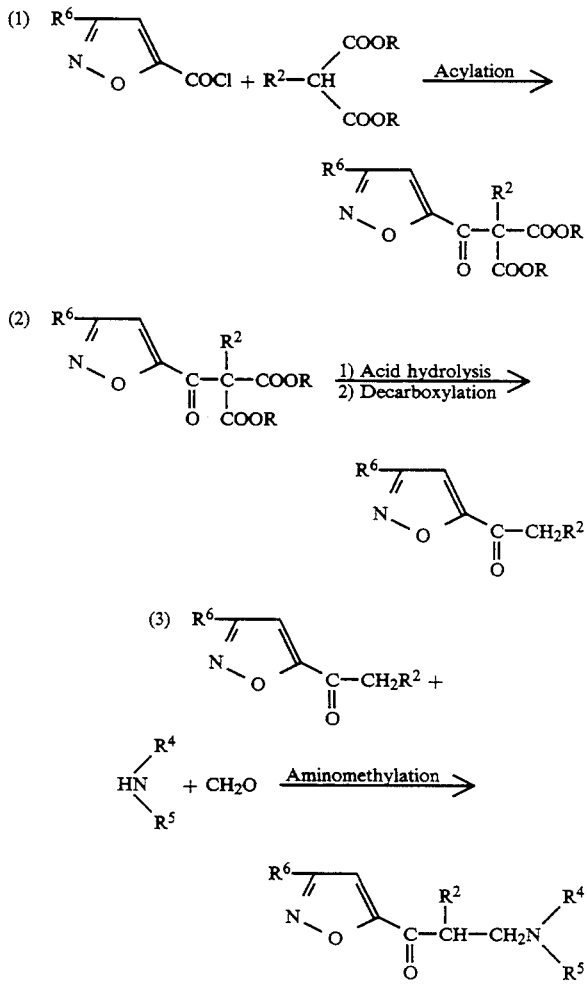

In the above preparation routes, $R^1$ to $R^6$ have the same meanings as defined above with respect to the formula (I), and R represents an ester residue.

The aminoketone derivatives of the formula (I) in which $R^1$ represents

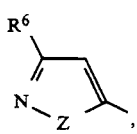

Z being an oxygen atom, and $R^3$ is a hydrogen atom can be produced by the following processes A–C:

Process A

The process A uses the steps (1)–(4) of the above-described preparation route A.

The step (1) in the process A can be conducted in the presence of a halogenating agent in a solvent at a temperature ranging from −30° C. to 100° C.

As the halogenating agent, chlorine, N-chlorosuccinimide or the like can be used.

Examples of the solvent include halogenated hydrocarbons such as chloroform, methylene chloride, 1,2-dichloroethane, and the like; ethers such as diethyl ether, diisopropyl ether and the like; aromatic hydrocarbons such as benzene, toluene and the like; dimethylformamide; and ethyl acetate.

The reaction can easily proceed by adding a base such as pyridine or the like.

The step (2) for cyclization can be conducted in the presence of a base in a solvent at a temperature ranging from −10° C. to 150° C.

Examples of the bases include organic bases such as triethylamine, pyridine, N,N-dimethylaniline and the like; and inorganic bases such as sodium hydrogencarbonate, potassium hydrogencarbonate, sodium carbonate, potassium carbonate, sodium hydroxide, potassium hydroxide and the like.

Examples of the solvent include ethers such as diethyl ether, tetrahydrofuran, diisopropyl ether and the like; aromatic hydrocarbons such as benzene, toluene, xylene and the like; halogenated hydrocarbons such as chloroform, dichloromethane, 1,2-dichloroethane; dimethylformamide; and dimethyl sulfoxide.

The step (3) can be conducted in the presence of an oxidizing agent in a solvent at a temperature ranging from −20° C. to 100° C.

As the oxidizing agent, chromic acid or pyridinium chlorochromate can be used. Chromic acid may be dissolved in water or an aqueous solution of acetic acid or sulfuric acid for use.

Examples of the solvent include water, acetic acid, propionic acid, acetone, methyl ethyl ketone, halogenated hydrocarbons such as chloroform, dichloromethane, 1,2-dichloroethane and the like.

The step (4) can be conducted in a solvent at a temperature ranging from −10° C. to 50° C.

Examples of the solvent include alcohols such as methanol, ethanol, isopropyl alcohol, amyl alcohol, isoamyl alcohol and the like; halogenated hydrocarbons such as chloroform, dichloromethane and the like; dioxane; tetrahydrofuran; and acetic acid.

The reaction can preferably proceed by adding an acid such as acetic acid, oxalic acid, hydrochloric acid, phosphoric acid, sulfuric acid, p-toluenesulfonic acid or the like.

The amine, which is reacted with the ketone derivative, may be used in the form of a corresponding hydrochloride.

Process B

The process B uses the steps (1)–(3) of the above-described preparation route B.

In this process, the step (1), in which R is a pyranyl group, can be conducted in a solvent at a temperature ranging from −20° C. to 100° C.

As the solvent, aromatic hydrocarbons such as benzene, toluene and the like can be used.

A sodium salt of the resulting malonic acid ester can be obtained by adding sodium hydride or metallic sodium.

The step (2) can be conducted in the presence of an acid in a solvent at a temperature ranging from 30° C. to 150° C.

As the solvent, aromatic hydrocarbons such as benzene, toluene, xylene and the like can be used.

Examples of the acid include p-toluenesulfonic acid, acetic acid, sulfuric acid and the like.

The step (3) can be conducted under the same condition as that in the step (4) in the process A.

Process C

The process C includes the following steps (1)–(3):

Step (1)

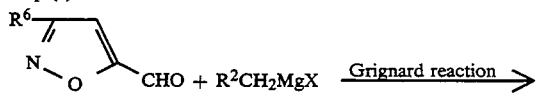

In this step, X represents a chlorine, bromine or iodine atom.

The step (1) can be conducted in a solvent at a temperature ranging from −78° C. to 50° C.

Examples of the solvent include ethers such as diethyl ether, tetrahydrofuran, dioxane and the like; and aromatic hydrocarbons such as benzene, toluene and the like.

Step (2)

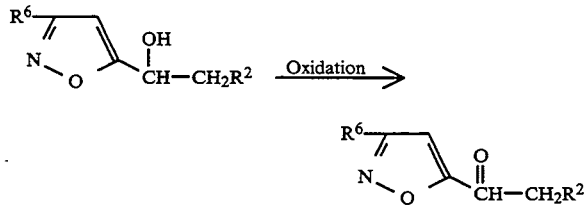

This step can be conducted under the same condition as that in the step (3) of the process A.

Step (3)

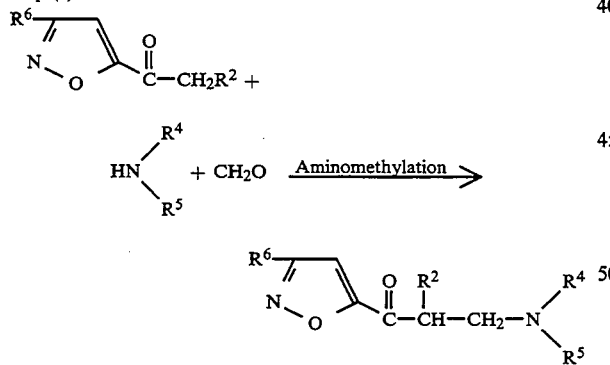

This step can be conducted under the same condition as that in the step (4) of the process A.

The aminoketone derivatives of the formula (I) in which $R^1$ is

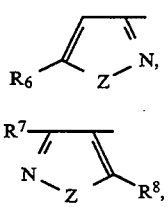

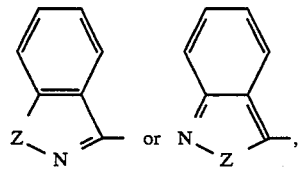

and $R^3$ is a hydrogen atom can be produced by a process including the following steps:

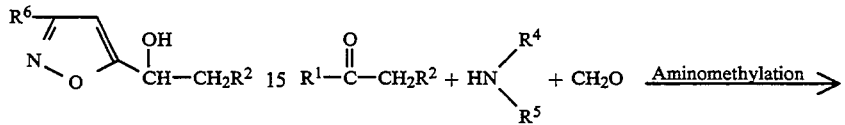

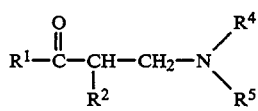

This step can be conducted under the same condition as that in the step (4) of the process A.

The aminoketone derivatives of the formula (I), in which $R^1$ is

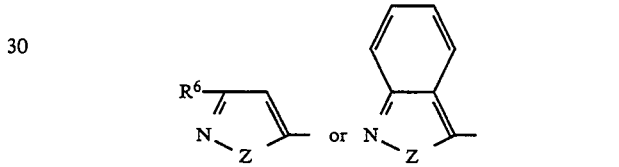

and $R^3$ is a lower alkyl group, or $R^2$ and $R^3$ are coupled together to form a five- or six-membered alicyclic group, can be produced by a process including the following step;

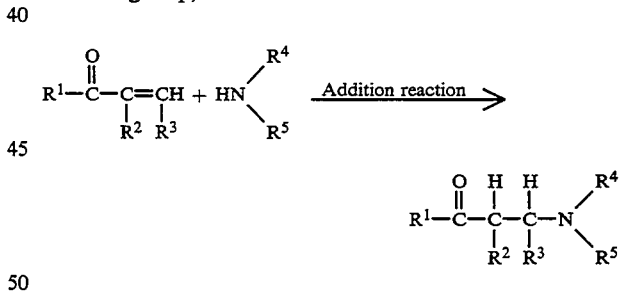

This step can be conducted in a non-solvent manner or in a solvent at a temperature ranging from −20° C. to 50° C.

Examples of the solvent include ketones such as acetone, methyl ethyl ketone and the like; ethers such as diethyl ether, tetrahydrofuran, dioxane and the like; halogenated hydrocarbons such as chloroform, methylene chloride, 1,2-dichloroethane and the like; aromatic hydrocarbons such as benzene, toluene and the like; and ethyl acetate.

The acid-addition salt of the aminoketone derivative of the formula (I) can be produced by a process including the step of reacting the aminoketone derivative with an acid.

The reaction can be conducted, for example, by reacting a solution of the aminoketone derivative with hydrogen chloride gas or a solution containing hydrochloric acid or fumaric acid.

Examples of the solvent to prepare the solutions include halogenated hydrocarbons such as chloroform, dichloromethane, 1,2-dichloroethane and the like; alcohols such as methanol, ethanol, isopropyl alcohol and the like; ethers such as diethyl ether, tetrahydrofuran, dioxane and the like; ethyl acetate; acetone; methyl ethyl ketone; water; and dimethylformamide.

The reaction temperature may range from −20° C. to 50° C.

The dosage of each aminoketone derivative of the invention to a patient varies depending on the symptom to be treated and the manner of administration. However, their daily dosage may generally range from 5–1,000 mg, preferably 50–300 mg per adult.

They can be administered orally or parenterally in the form of an oral preparation such as capsules, tablets, fine granules, syrups or powders or in the form of a parenteral preparation such as injections, suppositories or ointment.

As additives including pharmaceutically acceptable carriers and diluents for the formation of dosable preparations, excipients such as lactose, corn starch, sugar, sorbit and calcium phosphate, binders such as syrup, gum arabic, gelatin, sorbit, polyvinylpyrrolidone and hydroxypropylcellulose, lubricants such as magnesium stearate, talc, polyethylene glycol and silica, disintegrants such as potato starch and carboxymethylcellulose, wetting agents such as sodium laurylsulfate, etc. can be used suitably depending on each preparation form.

The present invention provides (+)-3-phenyl-5-[2-(1-pyrrolidinylmethyl ) butyryl ]isoxazole represented by the formula (1)

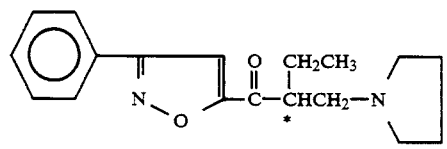

(1)

and a method for preparing optically active 3-phenyl-5-[2-(1-pyrrolidinylmethyl)butyryl]isoxazole and its salt which comprises the steps of reacting 3-phenyl-5-[2-(1-pyrrolidinylmethyl)butyryl]isoxazole with optically active sulfonic acid, particularly optically active 10-camphorsulfonic acid in a solvent; predominantly crystallizing one salt of the resultant two kinds of diastereomer salts out of the solvent to achieve resolution; and then demineralizing the respective diastereomer salts to isolate optically active 3-phenyl-5-[2-(1-pyrrolidinylmethyl)butyryl]isoxazole.

The preparation method of the present invention can be performed, for example, by the following procedure. That is, 3-phenyl-5-[2-(1-pyrrolidinylmethyl)butyryl]isoxazole is reacted with optically active 10-camphorsulfonic acid in a suitable solvent to produce two kinds of diastereomer salts, and the solvent is then concentrated or cooled, or another solvent which can decrease solubility may be added, to crystallize the slightly soluble diastereomer salt and to thereby separate the solid. The resultant salts of optically active 3-phenyl-5-[2-(1-pyrrolidinylmethyl)butyryl]isoxazole and optically active 10-camphorsulfonic acid are demineralized by using a suitable alkali to isolate optically active 3-phenyl-5-[2-(1-pyrrolidinylmethyl)butyryl]isoxazole.

No particular restriction is put on the solvent which can be used in the present invention, so long as the solvent can dissolve 3-phenyl-5-[2-(1-pyrrolidinylmethyl)-butyryl]isoxazole and optically active 10-camphorsulfonic acid and which permits the formation of the diastereomer salts and which can dissolve the easily soluble and slightly soluble diastereomer salts between room temperature and their boiling points and which allows the slightly soluble diastereomer salt to crystallize by concentration, cooling or the addition of another solvent. Preferable examples of the solvent include ketones such as acetone, methyl ethyl ketone and methyl isobutyl ketone as well as alcohols such as methanol, ethanol, propanol and isopropanol, and particularly preferable examples of the solvent include alkyl acetates such as methyl acetate, ethyl acetate and butyl acetate. Above all, ethyl acetate is most preferable from the viewpoint of a resolution yield.

In this case, the amount of the solvent is in the wide range of from 1.0 to 50 times (V/W) as much as that of 3-phenyl-5- [2- ( 1-pyrrolidinylmethyl) butyryl]isoxazole, and preferably, it is in the range of from about 1 to about 30 times (V/W).

No particular restriction is put on the ratio of 3-phenyl-5-[2-(1-pyrrolidinylmethyl) butyryl]isoxazole to optically active 10-camphorsulfonic acid, so long as the ratio is 1 or more equivalents of the latter per equivalent of the former. Nevertheless, the ratio is preferably 1.5 to 3 equivalents, more preferably 2 equivalents of the latter per equivalent of the former. In this case, when D-10-camphorsulfonic acid is used, (−)-3-phenyl-5-[2-(1pyrrolidinylmethyl)butyryl] isoxazole crystallizes as a slightly soluble diastereomer salt, and when L-10-camphorsulfonic acid is used, (+) -3-phenyl-5- [2- (1 -pyrrolidinylmethyl)butyryl] isoxazole crystallizes as a slightly soluble diastereomer salt.

No particular restriction is put on a temperature at which the diastereomer salt can be formed, but the temperature is preferably from room temperature to 50° C. A crystallization time is from about 1 to about 50 hours, preferably about 2 to about 30 hours.

Furthermore, the crystallization temperature should be below the boiling point or less of the solvent, and it is particularly preferably in the range of from −10° to 40° C.

Examples of the above-mentioned other solvent which can decrease the solubility include hexane and ethers.

The demineralization of the obtained diastereomer salt can be preferably carried out at a temperature of from 0° to 30° C. in the presence of sodium bicarbonate, potassium bicarbonate, sodium carbonate, potassium carbonate, dilute sodium hydroxide, dilute potassium hydroxide, ammonia or the like in water. The amount of the alkali to be used should be 2 equivalents or more per equivalent of the diastereomer salt.

The isolation of optically active 3-phenyl-5-[2-( 1-pyrrolidinylmethyl)butyryl]isoxazole from the resolving solution can be achieved by extracting the same with a non-hydrophilic solvent such as an ether, an alkyl acetate ester, chloroform, methylene chloride or hexane, and then distilling off the solvent.

The conversion of optically active 3-phenyl-5-[2-(1-pyrrolidinylmethyl)butyryl]isoxazole into an acid addition salt can be achieved by dissolving optically active 3-phenyl-5-[2-(1-pyrrolidinylmethyl)butyryl]isoxazole in an ether, an alkyl acetate ester, chloroform, methylene chloride, hexane or the like; adding 1 equivalent or more, preferably 1 to 10 equivalents of a mineral acid such as hydrochloric acid, nitric acid and sulfuric acid, or an organic acid such as acetic acid, oxalic acid, benzene-sulfonic acid or methanesulfonic acid; and then distilling off the solvent and the excess acid or collecting a crystallized salt of optically active 3-phenyl-5-[2-(1-pyrrolidinylmethyl)butyryl]isoxazole by filtration. Alternatively, the above-mentioned conversion into the acid addition salt can be achieved by extracting the above-mentioned organic solvent solution of optically active 3-phenyl-5-[2-(1-pyrrolidinylmethyl)butyryl]isoxazole with the above-mentioned mineral acid or organic acid; extracting the resultant aqueous solution again with an organic solvent such as chloroform in which an acid addition salt can be dissolved; distilling off the solvent from the solution or adding an organic solvent such as an ether, an alkyl acetate ester or hexane in which the acid addition salt of optically active 3-phenyl-5-[2-(1-pyrrolidinylmethyl) butyryl]isoxazole is scarcely soluble, to crystallize the acid addition salt; and then collecting the crystals by filtration.

The optically active compounds which can be obtained by the above-mentioned method are as follows:

(+)-3-phenyl-5-[2-(1-pyrrolidinylmethyl)butyryl]isoxazole and its salts.

(−)-3-phenyl-5-[2-(1-pyrrolidinylmethyl)butyryl]isoxazole and its salts.

The dose of the optically active aminoketone derivative of the present invention to each patient in need of a medical treatment is usually from 5 to 1000 mg, preferably from 10 to 300 mg to an adult per day, depending upon a symptom to be treated and an administration manner. The medicine can take any form of capsules, tablets, granules, syrup and powder which can be orally administered, and injections and suppositories which can be orally and parenterally administered. Examples of additives for the medicine include excipients (lactose, corn starch, sugar, sorbitol, calcium phosphate and the like), binders (syrup, gum arabic, gelatin, sorbitol, polyvinylpyrrolidone, hydroxypropyl cellulose and the like), glazing agents (magnesium stearate, talc, polyethylene glycol, silica and the like), disintegrators (potato starch, carboxymethyl cellulose and the like), and lubricants (sodium lauryl sulfate and the like). These additives can be used suitably in compliance with the form of the medicine.

EXAMPLE 1

5-(2-methyl-3-piperidinopropionyl)-3-phenylisoxazole hydrochloride (1) 5-(1-Hydroxypropyl)-3-phenylisoxazole Dissolved in 200 ml of benzene were 18.5 g (0.12 mol) of benzenehydroxamic acid chloride synthesized in accordance with a known process [J.Org.Chem., 45, 3916 (1980)] and 10.0 g (0.12 mole) of 1-pentyne-3-ol, followed by the dropwise addition of 18 g (0.18 mol) of triethylamine under ice cooling. After they were reacted under reflux for 10 hours, the reaction mixture was washed with water and the organic layer was dried over anhydrous sodium sulfate. The solvent was distilled off under reduced pressure. The resulting residue was purified by chromatography on a silica gel column (eluent: chloroform), whereby 5-(1-hydroxypropyl)-3-phenylisoxazole was obtained as colorless crystals. Analytical results of the crystals obtained: Yield: 19.3 g (79.7%). Melting point: 101°–102° C.

NMR (δ ppm,CDCl$_3$):1.0(3H,t,J=8 Hz), 1.6–2.2(2H,m), 3.1(1H,bs), 4.9(1H,t,J=6 Hz), 6.5(1H,s), 7.3–7.6(3H,m), 7.7–7.9(2H,m).

(2) 5-Propionyl-3-phenylisoxazole

In 130 ml of acetic acid, 19 g (93.6 mmol) of 5-(1-hydroxypropyl)-3-phenylisoxazole were dissolved. A solution which had been obtained by dissolving 6.4 g (64 mmol) of chromic acid in a mixed solution of 50 ml of acetic acid and 10 ml of water was added dropwise. The reaction mixture was heated at 60° C. for 3 hours and the solvent was distilled off under reduced pressure. The residue thus obtained was poured in ice water. Colorless crystals precipitated were collected by filtration and then dried under reduced pressure. The crystals were purified by chromatography on a silica gel (eluent:2:8 hexane/chloroform), whereby 5-propionyl-3-phenylisoxazole was obtained as colorless crystals. Analytical results of the crystals obtained: Yield: 17.5 g (93.2%). Melting point: 111°–112° C.

NMR (δ ppm, CDCl$_3$):1.3(3H,t,J=8 Hz), 3.1(2H,q,J=8 Hz), 7.2(1H,s), 7.5–8.0(5H,m).

(3) 5-(2-methyl-3-piperidinopropionyl)-3-phenylisoxazole hydrochloride

Added to 7.5 ml of dioxane were 5.0 g (24.9 mmol) of 5-propionyl-3-phenylisoxazole, 3.3 g (27.3 mmol) of piperidine hydrochloride and 1.2 g (40 mmol) of paraformaldehyde. 12N-Hydrochloric acid (0.105 ml) was added to the resultant mixture, followed by heating under reflux for 2 hours. After completion of the reaction, 50 ml of ethyl acetate were added. The mixture thus obtained was ice-cooled, and a white solid precipitated was collected by filtration. The thus-obtained white solid was added to 100 ml of a saturated solution of sodium bicarbonate, whereby the reaction product was converted into the free base. The free base was then extracted with ether. The ether layer was dried over anhydrous sodium sulfate. Under reduced pressure, the solvent was distilled off so that 5-(2-methyl-3-piperidinopropionyl)-3-phenylisoxazole was obtained as white crystals. Analytical results of the crystals obtained: Yield: 3.7 g (49.9%). Melting point: 114–116° C.

NMR (δ ppm,CDCl$_3$):1.3(3H,d,J=6 Hz), 1.5–1.8(6H,m), 3.5–4.0(1H,m), 7.2(1H,s), 7.5–7.7(3H,m), 7.7–8.0(2H,m).

The above white crystals (3.7 g) were dissolved in 80 ml of ether and HCl gas was introduced thereinto. A white solid precipitated was collected by filtration and then dried, whereby the hydrochloride was obtained. Analytical results of the hydrochloride obtained: Yield: 3.9 g (93.9%). Melting point: 161°–162° C. Elemental analysis data: Shown in Table 1.

EXAMPLES 2–6

The compounds shown in Table 1 were obtained in a similar manner to Example 1 except that in place of the piperidine hydrochloride in Example 1-(3), corresponding amine hydrochloride was used for the introduction of the respective

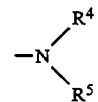

residue shown in Table 1. The analytical results of the individual compounds thus obtained are shown in Table 1.

TABLE 1

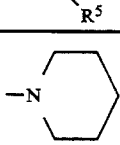

| Ex. | R² | -N(R⁴)(R⁵) | Molecular formula | Melting point (°C.) | Elemental analysis data (%) Calculated (upper) Found (lower) | | | |
|---|---|---|---|---|---|---|---|---|
| | | | | | C | H | N | Cl |
| 1 | —CH₃ | piperidinyl | C₁₈H₂₂N₂O₂.HCl | 161–162 | 64.57 / 63.51 | 6.92 / 7.31 | 8.37 / 8.19 | 10.59 / 10.67 |
| 2 | —CH₃ | pyrrolidinyl | C₁₇H₂₂N₂O₂.HCl | 119–121 | 63.25 / 63.29 | 7.18 / 7.52 | 8.68 / 8.54 | 10.98 / 10.94 |
| 3 | —CH₃ | morpholinyl | C₁₇H₂₀N₂O₃.HCl | 164–165 | 60.62 / 60.26 | 6.28 / 6.39 | 8.32 / 7.95 | 10.53 / 10.73 |
| 4 | —CH₃ | hexamethyleneimino | C₁₉H₂₄N₂O₂.HCl | 151–152 | 65.41 / 65.35 | 7.22 / 7.45 | 8.03 / 8.04 | 10.16 / 10.43 |
| 5 | —CH₃ | azetidinyl | C₁₇H₂₀N₂O₂.HCl | 139–141 | 63.65 / 62.56 | 6.60 / 6.50 | 8.73 / 8.67 | 11.05 / 11.02 |
| 6 | —CH₃ | 2-methylpiperidinyl | C₁₉H₂₄N₂O₂.HCl | 85–87 | 65.41 / 64.98 | 7.22 / 7.53 | 10.16 / 10.02 | 8.03 / 8.33 |

EXAMPLE 7

3-(4-Methoxyphenyul)-5-{2-methyl-3-(1-pyrrolidinyl)-propionyl} isoxazole hydrochloride (1) 4-Methoxybenzhydroxamic acid chloride A solution of 25 g (0.18 mol) of 4-methoxybenzaldehyde in 100 ml of ethanol was added dropwise under ice cooling to a solution of 15.3 g (0.22 mol) of hydroxylamine hydrochloride and 11.0 g (0.28 mol) of sodium hydroxide in 100 ml of water. After completion of the dropwise addition, the resulting mixture was stirred at room temperature for 30 minutes and ethanol was distilled off under reduced pressure. An insoluble solid was then collected by filtration. The solid was washed with water and hexane. The washings were combined with the filtrate. The organic layer was washed with water and dried over anhydrous magnesium sulfate. The solvent was distilled off, whereby 4-methoxybenzaldoxime was obtained as a colorless liquid. Its yield was 23.7 g (85%). It was then provided for the next reaction without further purification.

Dissolved in 65 ml of dimethylformamide were 6.5 g (43 mmol) of 4-methoxybenzaldoxime, followed by the gradual addition of 6.3 g (47 mmol) of N-chlorosuccinimide at room temperature. After the resultant mixture was stirred for 3 hours, 300 ml of water were added to the reaction mixture. The mixture thus formed was extracted with ethyl ether. The ether layer was washed with saturated saline and then dried over anhydrous magnesium sulfate. The solvent was distilled off, whereby 4-methoxybenzhydroxamic acid chloride was obtained. Analytical results of the compound obtained: Yield: 7.98 g (100%).

NMR (δ ppm,CDCl₃):3.80(3H,s), 6.85(2H,d,J=8 Hz), 7.74(2H,d,J=8 Hz), 10.23(1H,bs).

(2) 5-(1-Hydroxypropyl)-3-(4-methoxyphenyl)isoxazole

To a solution of 79.8 g (43 mmol) of 4-methoxybenzhydroxamic acid chloride and 7.23 g (86 mmol) of 1-pentyn-3-ol in 160 ml of benzene, a solution of 6.53 g (64.5 mmol) of triethylamine in 80 ml of benzene was added dropwise while maintaining the internal temperature at 3°–5° C. After the mixture was stirred for 2 hours, water was added so that the reaction product was extracted in the organic layer. The organic layer was separated and collected and the solvent was distilled off, whereby an oily residue was obtained. The oily residue was purified by silica gel chromatography (eluent: 30:1 chloroform/methyl alcohol), so that the title compound was obtained as yellow oil [yield: 8.07 g (81%)].

(3) 3-(4-Methoxyphenyl)-5-propionylisoxazole

Added to 160 ml of dichloromethane were 8.07 g (34.6 mmol) of 5-(1-hydroxypropyl)-3-(4-methoxyphenyl)isoxazole prepared in the above procedure (2), 4.83 g (58.9 mmol) of sodium acetate and 12.7 g of "Florisil" (trade mark, Wakojunyaku Inc.). While the resultant mixture was stirred vigorously, 12.7 g (58.9 mmol) pyridinium chlorochromate were added in small portions. After the mixture was stirred at room temperature for 4 hours, an insoluble material was filtered off and the solvent was distilled off. The residue was recrystallized from n-hexane, whereby 3-(4-methoxyphenyl)-5-propionylisoxazole was colorless crystals. Analytical results of the crystals obtained: Yield: 5.73 g (72%). Melting point: 135°–136° C.

NMR (δ ppm,CDCl$_3$):1.23(3H,t,J=7.2 Hz), 3.00(2H,q,J=7.2 Hz), 3.83(3H,s), 6.93(2H,d,J=8.8 Hz), 7.08(1H,s), 77.3(2H,d,J=8.8 Hz) .

(4) 3-(4-Methoxyphenyl)-5-{2-methyl-3-(1-pyrrolidinyl)-propionyl}isoxazole

Added to a mixed solvent of 22 ml of ethyl alcohol and 5 ml of dichloromethane were 2.22 g (9.61 mmol) of 3-(4-methoxyphenyl)-5-propionylisoxazole, 0.96 ml of a 37% aqueous formaldehyde solution and 1.37 g (19.2 mmol) of pyrrolidine, followed by stirring at room temperature for 8 hours. Water and ethyl ether were added, and the resultant mixture was acidified with 2N-hydrochloric acid. The water layer was separated and collected. After the water layer was alkalinized with an aqueous solution of pottasium hydroxide, dichloromethane was added for extraction. The solvent was distilled off, whereby 3-(4-methoxyphenyl)-5-{2-methyl-3-(1-pyrrolidinyl)propionyl} isoxazole was obtained as colorless crystals. Analytical results of the crystals obtained: Yield: 1.73 g (57%). Melting point: 75°–77° C.

NMR (δ ppm,CDCl$_3$):1.27(3H,d,J=6.8 Hz), 1.45–2.04(4H,m), 2.24–3.28(6H,m), 3.33–4.00(1H,m), 3.88(3H,s), 7.00(2H,d,J=8.8 Hz), 7.19(1H,s), 7.80(2H,d,J=8.8 Hz).

The above crystals were dissolved in ethyl acetate and then added to a 4N-hydrochloric acid-dioxane solution. The resulting hydrochloride was collected by filtration.

The analytical results of the hydrochloride thus obtained are shown in Table 2.

Examples 8–17

The compounds shown in Table 2 were obtained in a similar manner to Example 7 except for the use of $R^6$-introducing benzaldehyde derivatives (0.18 mol) shown in Table 2 in place of 4-methoxybenzaldehyde in Example 7-(1) and the

(19.2 mmol) , which were for the introduction of the

given in Table 2, in lieu of pyrrolidine in Example 7-(4). The analytical results of the respective compounds thus obtained are shown in Table 2.

TABLE 2

$$R^6-\underset{N\diagdown O}{\overset{\|}{C}}-\underset{\|}{\overset{}{C}}-\underset{\overset{|}{CH_3}}{CH}CH_2-N\diagup^{R^4}_{R^5}$$

| Ex. | $R^6$ | $-N\diagup^{R^4}_{R^5}$ | Molecular formula | Melting point (°C.) | Elemental analysis data (%) Calculated (upper) Found (lower) | | | |
|---|---|---|---|---|---|---|---|---|
| | | | | | C | H | N | Cl |
| 7 | CH$_3$O-⟨◯⟩- | -N⟨ ⟩ | C$_{18}$H$_{22}$N$_2$O$_3$.HCl.0.6H$_2$O | 141–144 | 59.78 59.55 | 6.74 6.68 | 7.75 7.87 | 9.80 10.27 |
| 8 | ⟨◯⟩- (CH$_3$O meta) | -N⟨ ⟩ | C$_{18}$H$_{22}$N$_2$O$_3$.1.3HCl.0.3H$_2$O | 101–105 | 58.88 58.36 | 6.56 6.95 | 7.63 8.49 | 12.55 12.60 |
| 9 | CH$_3$-⟨◯⟩- | -N⟨ ⟩ | C$_{18}$H$_{22}$N$_2$O$_2$.1.1HCl.0.5H$_2$O | 147–148 | 62.22 62.27 | 6.99 7.00 | 8.06 8.46 | 11.22 11.27 |

TABLE 2-continued $$R^6-\underset{N-O}{C}=\underset{O}{\overset{CH_3}{C}}-\overset{CH_3}{\underset{|}{C}H}CH_2-N\overset{R^4}{\underset{R^5}{\diagdown}}$$

| Ex. | R⁶ | —N(R⁴)(R⁵) | Molecular formula | Melting point (°C.) | Elemental analysis data (%) Calculated (upper) Found (lower) | | | |
|---|---|---|---|---|---|---|---|---|
| 10 | 2-methylphenyl | piperidino | C₁₈H₂₂N₂O₂·1.2HCl·0.5H₂O | 89–91 | C 61.57 / 60.76 | H 6.95 / 7.69 | N 7.98 / 9.01 | Cl 12.12 / 13.19 |
| 11 | 4-chlorophenyl | piperidino | C₁₇H₁₉ClN₂O₂·HCl·H₂O | 134–137 | C 54.70 / 54.33 | H 5.94 / 6.07 | N 7.50 / 7.25 | Cl 18.99 / 18.39 |
| 12 | 2-chlorophenyl | piperidino | C₁₇H₁₉ClN₂O₂·HCl | 130–132 | C 57.48 / 57.12 | H 5.67 / 5.70 | N 7.89 / 7.82 | Cl 19.96 / 19.66 |
| 13 | 4-fluorophenyl | piperidino | C₁₇H₁₉FN₂O₂·HCl | 149–150 | C 60.27 / 59.95 | H 5.95 / 6.02 | N 8.27 / 8.24 | F 5.61 / 5.32, Cl 10.46 / 10.31 |
| 14 | 4-CF₃-phenyl | piperidino | C₁₈H₁₉F₃N₂O₂·1.1HCl | 140–142 | C 55.64 / 56.13 | H 5.51 / 5.25 | N 6.96 / 6.95 | F 14.15 / 13.62, Cl 8.80 / 9.03 |
| 15 | 3-CF₃-phenyl | piperidino | C₁₈H₁₉F₃N₂O₂·1.5HCl·H₂O | 90–92 | C 51.96 / 51.78 | H 5.21 / 6.09 | N 6.73 / 7.89 | F 13.70 / 11.18, Cl 12.78 / 12.42 |
| 16 | 4-NO₂-phenyl | piperidino | C₁₇H₁₉N₃O₄·HCl·0.5H₂O | 140–142 | C 54.48 / 54.70 | H 5.65 / 5.68 | N 11.21 / 10.83 | Cl 9.46 / 8.99 |
| 17 | 3-NO₂-phenyl | piperidino | C₁₈H₂₁N₃O₄·HCl | 195–200 | C 56.91 / 56.82 | H 5.64 / 5.95 | N 11.06 / 10.90 | Cl 9.33 / 9.18 |

EXAMPLE 18

3-Bromo-5-(2-methyl-3-piperidinopropionyl)isoxazole hydrochloride (1) 3-Bromo-5-(1-hydroxypropyl) isoxazole Added to 800 ml of ethyl acetate were 8 ml of water, 60.0 g (0.6 mol) of potassium hydrogencarbonate and 73.5 g (0.88 mol) of 1-pentyn-3-ol. Under stirring, 40.5 g (0.2 mol) of dibromoformaldoxime were added at room temperature over 3 hours. After the resultant mixture was stirred at room temperature for 16 hours, water was added and the reaction product was extracted with ethyl acetate. Subsequent to concentration, 3-bromo-5-(1-hydroxypropyl) isoxazole was obtained as oil. It was distilled to collect a fraction at 97°–102° C./2 mmHg. Analytical results of the fraction obtained: Yield: 18 g (74%).

NMR (δ ppm,CDCl₃): 1.0(3H,t,J=7 Hz), 1.7–2.2(2H,m), 3.7(1H,bs), 4.8(1H,t,J=7 Hz), 6.3(1H,s).

(2) 3-Bromo-5-propionylisoxazole

Added to 100 ml of acetic acid were 15 g (73 mmol) of the alcohol derivative [3-bromo-5-(1-hydroxypropyl-)isoxazole] obtained in the above procedure (1), followed by the dropwise addition of a solution of 5.4 g (54 mmol) of chromic acid in an acetic acid-water solution (80 mf of acetic acid and 5.5 ml of water) while the internal temperature was maintained at 10°–15° C. After the resultant mixture was stirred at room temperature for 6 hours, the solvent was distilled off under reduced pressure and water and sodium hydrogencarbonate were added to alkalinize the mixture. Ethyl ether was added to extract the reaction product. The extract was concentrated so that 3-bromo-5-propionylisoxazole was obtained as colorless crystals. Analytical results of the crystals obtained: Yield: 12.0 g (81%). Melting point: 35°–37° C.

NMR (δ ppm,CDCl$_3$): 1.2(3H,t,J=7 Hz), 3.0(2H,q,J=7 Hz), 6.9(1H,s).

(3) 3-Bromo-5-(2-methyl-3-piperidinopropionyl)isoxazole hydrochloride

Using 3.0 g (14.7 mmol) of the ketone derivative (3-bromo-5-propionylisoxazole) prepared above in the procedure (2), 1.98 g (16.4 mmol) of piperidine hydrochloride and 0.72 g (24 mmol) of paraformaldehyde, a Mannich base was obtained as oil in a similar manner to Example 1-(3). The base was similarly converted to the hydrochloride, whereby 3-bromo-5-(2-methyl-3-piperidinopropionyl)isoxazole hydrochloride was obtained as colorless crystals. Analytical results of the hydrochloride obtained: Yield: 2.5 g (45%).

Its melting point and elemental analysis data are shown in Table 3.

EXAMPLE 19

3-Propyl-5-(2-methyl-3-piperidinopropionyl)isoxazole hydrochloride

(1) 3-Propyl-5-propionylisoxazole

Dissolved in 50 ml of chloroform were 5.0 g (57.5 mmol) of n-butylaldoxime and 0.3 ml of pyridine, to which 7.6 g (57.1 mmol) of N-chlorosuccinimide were added in small portions while the internal temperature was controlled not to exceed 35° C. After the addition, the resultant mixture was stirred at room temperature for 1 hour. To the solution, 6.0 g (71.4 mmol) of 1-pentyn-3-ol and 5.9 g (58.4 mmol) of triethylamine were added. The stirring was continued for 2 hours at 40°–50° C. After the solvent was distilled off under reduced pressure, water was added and the reaction product was then extracted with diethyl ether. After concentration, the residue was purified by silica gel chromatography (eluent: chloroform) so that 3-propyl-5-(1-hydroxypropyl)isoxazole was obtained. It was dissolved in acetone, oxidized with Jones' reagent under ice cooling, and purified by silica gel chromatography (eluent: chloroform), so that 3-propyl-5-propionylisoxazole was obtained as colorless oil. Analytical results of the oil obtained: Yield: 6.9 g (72%).

NMR (δ ppm,CDCl$_3$): 0.9–1.3(6H,m), 1.3–2.0(2H,m), 2.5–3.1(4H,m), 6.8(1H,s).

(2) 3-Propyl-5-(2-methyl-3-piperidinopropionyl)isoxazole hydrochloride

From 2.0 g (12 mmol) of 3-propyl-5-propionylisoxazole prepared above in the procedure (1), 1.7 g (14 mmol) of piperidine hydrochloride and 0.5 g (16.7 mmol) of paraformaldehyde, 3-propyl-5-(2-methyl-3-piperidinopropionyl)isoxazole hydrochloride was obtained as colorless crystals in a similar manner to Example 1-(3). Analytical results of the crystals obtained: Yield: 2.2 g (70%).

Its melting point and elemental analysis data are shown in Table 3.

EXAMPLE 20

3-(5-methyl-2-furfuryl-5-{2-methyl-3-(1-pyrrolidinyl)-propionyl}isoxazole hydrochloride

(1) 5-(1-Hydroxypropyl)-3-(5-methyl-2-furfuryl)-isoxazole

Following a known process [Tetrahedron, 40, 2985 (1984)], 2.9 g (21.5 mmol) of N-chlorosuccinimide were added at room temperature to a solution of 2.44 g (19.5 mmol) of 5-methyl-2-furfuralaldoxime and 0.8 ml of pyridine in 50 ml of chloroform. After the resultant mixture was stirred for 1 hour at room temperature, 3.3 g (39 mmol) of 1-pentyn-3-ol were added, followed by the dropwise addition of a solution of 2.9 g (29 mmol) of triethylamine in 25 ml of chloroform at 3°–5° C. The mixture thus obtained was stirred at room temperature for 1 hour, followed by the addition of water. The reaction product was extracted with chloroform. After the solvent was distilled off, the residue was purified by silica gel chromatography (eluent: 50:1 chloroform/methanol) so that 5-(1-hydroxypropyl)- 3 -(5 -methyl-2-furfuryl)isoxazole was obtained as yellow oil. Analytical results were as follows: Yield: 3.7 g (91%).

NMR (δ ppm,CDCl$_3$): 1.00(3H,t,J=7.6 Hz), 1.92(2H,d), 2.38(3H,bs), 4.80(1H,t,J=6.2 Hz), 6.10(1H,bd,J=3.0 Hz), 6.43(1H,s), 6.75 (1H,d,J=3.0 Hz).

(2) 3-(5-Methyl-2-furfuryl)-5-propionylisoxazole

To a solution of 3.67 g (17.7 mmol) of the alcohol derivative [5-(1-hydroxypropyl)-3-(5-(methyl-2-furfuryl)isoxazole]prepared above in the procedure (1) in 13 ml of dichloromethane, were added 2.47 g (30 mmol) of sodium acetate and 6.5 g (30 mmol) of pyridinium chlorochromate. The resultant mixture was stirred vigorously. After the mixture was stirred for 6 hours at room temperature, an insoluble material was filtered off, and the solvent was then distilled off so that 3-(5-methyl-2-furfuryl)-5-propionylisoxazole was obtained as colorless crystals. Analytical results of the crystals obtained: Yield: 1.52 g (42%). Melting point: 100°–103° C.

(3) 3-(5-Methyl-2-furfuryl)-5-{2-methyl-3-(1-pyrrolidinyl)-propionyl}isoxazole hydrochloride Added to 15 ml of ethyl alcohol were 1.52 g (7.4 mmol) of the ketone derivative [3-(5-methyl-2-furfuryl)-5-propionylisoxazole]prepared above in the procedure (2), 0.75 ml of a 37% aqueous solution of formaldehyde and 1.1 g (14.8 mmol) of pyrrolidine, followed by stirring at room temperature for 20 hours. The reaction mixture was added with 15 ml of 2N-hydrochloric acid and 20 ml of ethyl ether. After the mixture thus obtained was stirred, the water layer was separated and collected. The water layer was alkalinized with a solution of potassium hydroxide. The resultant solution was extracted with dichloromethane. The organic extract was dried over anhydrous magnesium sulfate and the solvent was then distilled off, whereby the title Mannich base, i.e., 3-(5-methyl-2-furfuryl)-5-{2-methyl-3- (1-pyrrolidinyl) propionyl}isoxazole was obtained as yellow oil. Analytical results were as follows: Yield: 1.3 g (61%) - Oil.

NMR (δ ppm,CDCl3): 1.27(3H,d,J=7.2 Hz), 1.43–2.17(4H,m), 2.27–3.33(6H,m), 2.40(3H,s), 3.40–3.97(1H,m), 6.12 (1H,bd,J=3.2 Hz), 6.83(1H,d,J=3.2 Hz), 7.07(1H,s).

The oily matter (1.3 g) obtained as described above was dissolved in 5 ml of ethyl acetate, followed by the addition of 2 ml of a 4N-hydrochloric acid-dioxane solution. The resultant solution was concentrated so that 3-(5-methyl-2-furfuryl)-5-{2-methyl-3-(1-pyrrolidinyl)propionyl}isoxazole hydrochloride was obtained as colorless crystals. Analytical results of the crystals obtained: Yield: 1.4 g (60%).

Its melting point and elemental analysis data are shown in Table 3.

EXAMPLE 21

3-Benzyl-5-(2-methyl-3-piperidinopropionyl)isoxazole hydrochloride (1) 3-Benzyl-5-(1-hydroxypropyl)isoxazole Using phenylacetohydroxamoyl chloride prepared in accordance with a known process (Gazetta Chimica Italiana, 110, 341 (1980); J. Org. Chem., 3.3, 476 (1968), the title compound was prepared in the following manner.

In 10 ml of dry diethyl ether, 2 g (12 mmol) of phenylacetohydroxamoyl chloride and 7 g (83 mmol) of 1-pentyne-3-ol were dissolved. While the resultant mixture was maintained at an internal temperature of 2°–5° C. under ice cooling, 1.27 g (12 mmol) of triethylamine were added dropwise. After the dropwise addition, the reaction mixture was heated under reflux for 1 hour. The reaction mixture was cooled and then poured into water. The reaction product was extracted with diethyl ether. After concentration, the reaction product was purified by silica gel chromatography (eluent: 5:1 n-hexane/ethyl acetate) so that 3-benzyl-5-(1-hydroxypropyl)isoxazole was obtained as colorless oil. Analytical results of the oily matter obtained: Yield: 1.9 g (73%).

NMR (δ ppm,CDCl3): 0.96(3H,t,CH3,J=8 Hz), 1.64–2.10(2H,m,CH2), 3.92(2H,s,CH2), 4.5–4.8(1H,m,CH), 5.92(1H,s), 7.24 (5H,bs, aromatic protons).

(2) 3-Benzyl-5-propionylisoxazole

Dissolved in 20 ml of acetone were 1.8 g (8.3 mmol) of the alcohol derivative [3-benzyl-5- (1-hydroxypropyl)isoxazole]prepared above in the procedure (1). Jones' oxidation was then conducted while the internal temperature was maintained at 4°–5° C. under ice cooling. The reaction was allowed to proceed until the light red color of an aqueous sulfuric acid solution of chromium(IV) oxide remained slightly. Isopropyl alcohol was added to the reaction mixture. After an insoluble material was filtered off, the solvent was distilled off. The residue was purified by silica gel chromatography (eluent: 9:1 n-hexane/ethyl acetate), whereby 3-benzyl-5-propionylisoxazole was obtained as colorless oil. Analytical results of the oily matter obtained: IR (γ cm$^{-1}$, neat): 2970, 1690, 1460, 920

(3) 3-Benzyl-5-(2-methyl-3-piperidinopropioyl)isoxazole hydrochloride

In 2 ml of dioxane, 1.5 g (7 mmol) of 3-benzyl-5-propionylisoxazole prepared above in the procedure (2), 0.93 g (7.7 mmol) of piperidine hydrochloride, 0.25 g (8.3 mmol) of paraformaldehyde and two droplets of 12N-hydrochloric acid were heated under reflux for 60 minutes. When left over in a cool place for 3 days after completion of the reaction, the reaction mixture became a solid. Diethyl ether was added to the solid. A solid was collected by filtration and then dried, whereby 3-benzyl-5-(2-methyl-3-piperidinopropionyl)isoxazole hydrochloride was obtained as colorless crystals. Analytical results of the crystals obtained: Yield: 1.6 g (73.5%).

Its melting point and elemental analysis data are shown in Table 3.

EXAMPLE 22

3-bezoyl-5-(Z-methyl-3-piperidinopropionyl)isoxazole hydrochloride (1) 3-benzoyl-5-propionylisoxazole Reacted under reflux for 2 hours were 5.0 g (27.3 mmol) of benzoylacetohydroxamoyl chloride prepared by a known process [J. Org. Chem., 409 (1942)]and 5.0 g (59.5 mmol) of 1-pentyne-3-ol. The reaction mixture was added into water, followed by extraction with ethyl ether. The extract was concentrated and then purified by silica gel chromatography (eluent: chloroform), whereby the title compound, namely, 3-benzoyl-5-(1-hydroxypropyl)isoxazole was obtained. It was dissolved in acetone, to which the Jones' reagent was added dropwise under ice cooling so that it was oxidized from the alcohol form to a ketone form. Isopropyl alcohol was added to the reaction mixture. After an insoluble material was filtered off, the solvent was distilled off so that 3-benzoyl-5-propionylisoxazole was obtained as colorless crystals. Analytical results of the crystals obtained: Yield: 4.9 g (77.6%). Melting point: 70°–71° C.

(2) 3-Benzoyl-5-(2-methyl-3-piperidinopropionyl)isoxazole hydrochloride

In 3 ml of dioxane, 2.0 g (8.7 mmol) of the ketone derivative (3-benzoyl-5-propionylisoxazole) prepared above in the procedure (1), 1.1 g (9.1 mmol) of piperidine hydrochloride, 0.32 g (10.7 mmol) of paraformaldehyde and two droplets of 12N-hydrochloric acid were heated under reflux for 60 minutes. After completion of the reaction, the reaction mixture was added with water and then extracted with diethyl ether. The water layer was alkalinized with an aqueous solution of sodium carbonate, followed by the extraction of the reaction product with ethyl ether. The extract was dried over anhydrous magnesium sulfate, and the solvent was distilled off to obtain an oily matter (1.5 g). The oily matter was dissolved in 5 ml of ethyl acetate, followed by the addition of 2 ml of a 4N-hydrochloric acid-dioxane solution under ice cooling. A matter precipitated was collected by filtration and washed with n-hexane, so that 3-benzoyl-5-(2-methyl-3-piperidinopropionyl) isoxazole hydrochloride was obtained as colorless crystals. Analytical results of the crystals obtained: Yield: 1.2 g (42%).

Its melting point and elemental analysis data are shown in Table 3.

EXAMPLES 23-27

As shown in Table 3, the compound of Example 23 was prepared in a similar manner to Example 19 except that acetoaldoxime was employed in place of n-butylaldoxime used in Example 19-(1). On the other hand, the compounds of Examples 24, 25, 26 and 27 were prepared in a similar manner to Example 20 except that thiophenealdoxime, 5-methyl-thiophene-2-aldoxime, pyridine-2-aldoxime and 5-ethyl-2-furfuralaldoxime were employed, respectively instead of 5-methyl-2-furfuralaldoxime used in Example 20-(1). The analytical results of the compounds thus obtained are shown in Table 3.

TABLE 3

| Ex. | $R^6$ | $-N\begin{smallmatrix}R^4\\R^5\end{smallmatrix}$ | Molecular formula | Melting point (°C.) | Elemental analysis data (%) Calculated (upper) Found (lower) | | | | |
|---|---|---|---|---|---|---|---|---|---|
| 18 | Br— |  | $C_{12}H_{17}BrN_2O_2 \cdot HCl$ | 161-163 | C 42.69 42.61 | H 5.37 5.59 | N 8.30 8.05 | Cl 10.50 10.62 | Br 23.67 23.01 |
| 19 | $C_3H_7$— |  | $C_{15}H_{24}N_2O_2 \cdot HCl$ | 134-136 | C 59.89 59.51 | H 8.38 8.38 | N 9.31 9.30 | Cl 11.79 11.48 | |
| 20 | 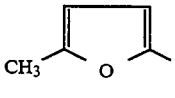 |  | $C_{16}H_{20}N_2O_3 \cdot HCl$ | 140-141 | C 59.16 58.55 | H 6.52 6.49 | N 8.63 8.62 | Cl 10.92 10.95 | |
| 21 | 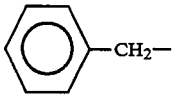 |  | $C_{19}H_{24}N_2O_2 \cdot HCl$ | 155-156 | C 65.41 63.48 | H 7.22 7.29 | N 8.03 7.97 | Cl 11.14 11.14 | |
| 22 | 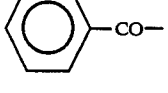 |  | $C_{19}H_{22}N_2O_3 \cdot HCl$ | 154-155 | C 62.89 59.78 | H 6.39 6.80 | N 7.72 7.80 | Cl 9.77 11.82 | |
| 23 | $CH_3$— |  | $C_{13}H_{20}N_2O_2 \cdot HCl$ | 178-180 | C 57.24 56.78 | H 7.76 7.54 | N 10.27 10.27 | Cl 13.00 13.33 | |
| 24 | 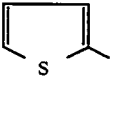 |  | $C_{15}H_{18}N_2O_2S \cdot HCl$ | 145-146 | C 53.07 53.57 | H 5.97 5.88 | N 8.25 8.40 | S 9.44 8.52 | Cl 11.49 11.97 |
| 25 | 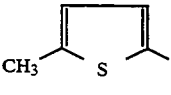 |  | $C_{16}H_{20}N_2O_2S \cdot HCl$ | 151-152 | C 55.20 54.91 | H 6.14 5.83 | N 8.05 7.83 | S 9.21 9.85 | Cl 12.22 12.25 |
| 26 | 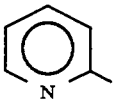 |  | $C_{16}H_{19}N_3O_2 \cdot C_4H_4O_4$ | 99-101 | C 59.84 59.13 | H 5.77 5.72 | N 10.47 10.28 | | |

TABLE 3-continued

[Structure: R⁶ group connected to isoxazole ring (N-O), with -C(=O)-C(CH₃)H-CH₂-NR⁴R⁵]

| Ex. | R⁶ | -NR⁴R⁵ | Molecular formula | Melting point (°C.) | Elemental analysis data (%) Calculated (upper) Found (lower) | | | |
|---|---|---|---|---|---|---|---|---|
| 27 | [isoxazole with -CH₂-O-CH(CH₃)- substituent] | pyrrolidinyl | $C_{17}H_{22}N_2O_3 \cdot HCl$ | 121–122 | C 60.26 59.37 | H 6.84 6.74 | N 8.27 8.16 | Cl 10.46 10.71 |

EXAMPLE 28

3-Phenyl-5-{2-(1-pyrrolidinylmethyl) butyryl}isoxazole hydrochloride

(1) 3-Phenyl-5-hydroxymethylisoxazole

Dissolved in 700 ml of chloroform were 100 g (0.72 mol) of benzhydroxamic acid chloride prepared in Example 1-(1) and 81 g (1.4 mol) of propargyl alcohol, followed by the dropwise addition of 87 g (0.86 mol) of triethylamine under ice cooling. After completion of the dropwise addition, the reaction mixture was stirred at 50° C. for 30 minutes. The reaction mixture was washed with water and the organic layer was dried over anhydrous magnesium sulfate. The solvent was distilled off. The residue was washed with a 10:1 mixed solvent of hexane and ethyl acetate, whereby 3-phenyl-5-hydroxymethylisoxazole was obtained as crystals. Analytical results of the crystals obtained: Yield: 100.6 g (80.0%). Melting point: 48°–50° C.

NMR (δ ppm,CDCl₃): 3.30(1H,bs), 4.78(2H,s), 6.52(1H,s), 7.16–7.57(3H,m), 7.57–7.97(2H,m).

(2) 3-Phenylisoxazole-5-carboxylic acid

In 1.5 l of water, 50 g (0.3 mol) of 3-phenyl-5-hydroxymethylisoxazole synthesized above in the procedure (1) and 13.7 g (0.34 mol) of sodium hydroxide were suspended. While the resultant suspension was maintained at 30° C., 72.2 g (0.46 mole) of potassium permanganate were added in three portions. The resultant mixture was then stirred at 50° C. for 30 minutes. Manganese dioxide formed were filtered off, and the filtrate was acidified with concentrated hydrochloric acid. A white solid formed was collected by filtration, washed with water and then dried under reduced pressure, whereby 3-phenylisoxazole-5-carboxylic acid was obtained. Analytical results of the carboxylic acid derivative obtained: Melting point: ≧250° C. (decomposed).

NMR (δ ppm,CDCl₃ +DMSO-d₆): 7.34(1H,bs), 7.40–7.74(3H,m) , 7.80–8.00 (2H,m) , 11.40( 1H, bs ).

(3) 3-Phenylisoxazole-5-carboxylic acid chloride

Added to 500 g (4.2 mol) of thionyl chloride were 110 g (0.58 mol) of 3-phenylisoxazole-5-carboxylic acid prepared above in the procedure (2), followed by the further addition of 2 ml of dimethylformamide. The resulting mixture was heated under reflux for 3 hours. After completion of the reaction, thionyl chloride was distilled off under reduced pressure, followed by the addition of 500 ml of benzene. When the mixture thus obtained was distilled under reduced pressure, the title compound, i.e., 3-phenylisoxazole-5-carboxylic acid chloride was obtained as a solid. It was provided for the next step without purification.

(4) 3-Phenyl-5-butyrylisoxazole

To 130 ml of benzene, were added 12.9 g (97.7 mmol) of ethylmalonic acid, 20.2 g (240.5 mmol) of 3,4-dihydropyran and 2 droplets of concentrated sulfuric acid. They were reacted for 1 hour under ice cooling, whereby dipyranyl ethylmalonate was prepared. The reaction mixture was added with 4.7 g (117.5 mmol) of 60% sodium hydride, followed by heating under stirring at 50° C. for 5 hours. A solution of 15.0 g (79.4 mmol) of 3-phenylisoxazole-5-carboxylic acid chloride, which had been synthesized above in the procedure (3), in 70 ml of tetrahydrofuran was added under ice cooling to the above-prepared reaction mixture. The mixture thus obtained was then subjected to a reaction at room temperature for 12 hours. The reaction mixture was added with 20 ml of acetic acid and then heated under reflux for 8 hours. The reaction mixture so obtained was poured into water and then extracted with benzene. The organic layer was washed successively with water, an aqueous solution of sodium hydrogencarbonate and saturated saline, and was then dried over anhydrous sodium sulfate. After the benzene was distilled off, hexane was added into the residue. Crystals precipitated was collected by filtration, so that 3-phenyl-5-butyrylisoxazole was obtained. Analytical results of the crystals obtained: Yield: 14.6 g (85.6%). Melting point: 90°–92° C.

NMR (δ ppm,CDCl₃): 0.8–1.2(3H,m), 1.4–2.1(2H,m), 3.0(2H,t,J=6 Hz), 7.1(1H,s), 7.2–7.6(3H,m), 7.6–8.0(2H,m).

(5) 3-Phenyl-5-{2-(1-pyrrolidinylmethyl)butyryl}isoxazole hydrochloride

In a similar manner to Example 1, 14 g (85.1 mmol) of 3-phenyl-5-butyrylisoxazole, 8.4 g (78.5 mmol) of pyrrolidine hydrochloride, 2.6 g (86.7 mmol) of paraformaldehyde and 20 droplets of concentrated hydrochloric acid were reacted in 20 ml of dioxane so that 3-phenyl-5-{2-(1-pyrrolidinylmethyl)-butyryl}isoxazole was obtained. Analytical results of the compound obtained: Yield: 13.4 g (69.1%) Melting point: 68°–69° C.

NMR (δ ppm,CDCl₃): 0.9(3H,t,J=7 Hz), 1.3–2.0(6H,m) , 2.8–3.7(7H,m), 7.2(1H,s), 7.2–7.6(3H,m), 7.6–8.0(2H,m).

The compound obtained as described above was dissolved in ethyl acetate in a similar manner to Example 22. The resulting solution was added dropwise to a 4N-hydrochloric acid-dioxane solution so that 3-phenyl-5-{2-(1-pyrrolidinylmethyl)butyryl}isoxazole hydrochloride was obtained as crystals.

The analytical results of the hydrochloride thus obtained are shown in Table 4.

EXAMPLES 29-35

The compounds shown in Table 4 were obtained in a similar manner to Example 28 except that hydrochlorides (78.5 mmol) capable of forming

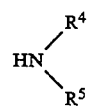

for the introduction of the respective

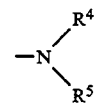

shown in Table 4 were employed, respectively in lieu of the pyrrolidine hydrochloride in Example 28-(5).

The analytical results of the respective compounds thus obtained are shown in Table 4.

TABLE 4

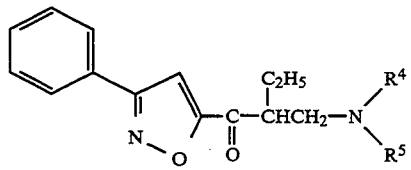

| Ex. | $-N\begin{smallmatrix}R^4\\R^5\end{smallmatrix}$ | Molecular formula | Melting point (°C.) | Elemental analysis data (%) Calculated (upper) Found (lower) | | | |
|---|---|---|---|---|---|---|---|
| | | | | C | H | N | Cl |
| 28 |  | $C_{18}H_{22}N_2O_2 \cdot HCl$ | 158–159 | 64.57<br>64.00 | 6.92<br>6.81 | 8.37<br>8.27 | 10.58<br>10.95 |
| 29 |  | $C_{19}H_{24}N_2O_2 \cdot HCl$ | 156–157 | 65.41<br>64.85 | 7.22<br>7.01 | 8.03<br>7.93 | 10.16<br>11.33 |
| 30 |  | $C_{18}H_{22}N_2O_3 \cdot HCl$ | 161–162 | 61.62<br>59.40 | 6.61<br>6.36 | 7.98<br>7.78 | 10.10<br>10.17 |
| 31 |  | $C_{20}H_{26}N_2O_2 \cdot HCl$ | 149–151 | 66.19<br>66.29 | 7.50<br>7.27 | 7.72<br>8.02 | 9.77<br>10.35 |
| 32 |  | $C_{25}H_{29}N_3O_2 \cdot 2HCl$ | 260–265 | 62.61<br>62.56 | 5.91<br>6.53 | 9.12<br>8.91 | 15.40<br>14.96 |
| 33 |  | $C_{26}H_{30}N_2O_2 \cdot 1.3HCl \cdot 0.5H_2O$ | 69–70 | 68.04<br>67.89 | 7.09<br>7.43 | 6.10<br>6.00 | 10.04<br>9.68 |
| 34 |  | $C_{19}H_{24}N_2O_2 \cdot HCl$ | 139–141 | 65.41<br>84.26 | 7.22<br>6.96 | 8.03<br>7.95 | 10.16<br>10.10 |

TABLE 4-continued

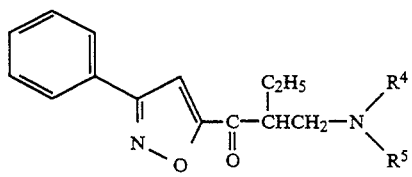

| Ex. | —N(R⁴)(R⁵) | Molecular formula | Melting point (°C.) | Elemental analysis data (%) Calculated (upper) Found (lower) | | | |
|---|---|---|---|---|---|---|---|
| | | | | C | H | N | Cl |
| 35 | —N(CH₃)(CH₃) | C₁₆H₂₀N₂O₂·HCl | 135–137 | 66.19 | 7.50 | 7.72 | 9.77 |
| | | | | 65.68 | 7.48 | 7.69 | 9.75 |

EXAMPLE 36

3- (4-Methylphenyl)-5-
{2-(1-pyrrolidinylmethyl)-butyryl}isoxazole
hydrochloride (1) 3-(4-Methylphenyl)-5-methoxycarbonylisoxazole Added to 100 ml of chloroform were 10.0 g (74.1 mmol) of 4-methylbenzaldoxime, 9.9 g (74.4 mmol) of N-chlorosuccinimde and 0.4 ml of pyridine. After N-chlorosuccinimide was completely dissolved, the resulting solution was stirred for further 30 minutes. Under ice cooling, 9.3 g (110.7 mmol) of methyl propionate and 9.0 g (89.1 mmol) of triethylamine were added. The resulting mixture was stirred at room temperature for 12 hours. The reaction mixture was added with water and then extracted with chloroform. The extract was treated by a method known per se in the art. Subsequent purification on a silica gel column (eluent: chloroform) gave 3-(4-methylphenyl)-5-methoxycarbonylisoxazole as crystals. Analytical results of the crystals obtained: Yield: 8.0 g (49.8%). Melting point: 106°–108° C.

NMR (δ ppm,CDCl₃): 2.4(3H,s) , 4.0(3H,s) , 7.1(1H,s), 7.2–7.3(2H,m), 7.6–7.8(2H,m).

(2) 3- (4-Methylphenyl) isoxazole-5-carboxylic acid

In a mixture consisting of 160 ml of ethanol and 80 ml of water, 8.0 g (36.9 mmol) of the methyl ester derivative [3-(4-methylphenyl)-5-methoxycarbonylisoxazole] prepared above in the procedure (1) were hydrolyzed with 4.2 g (75.0 mmol) of potassium hydroxide at room temperature. The reaction mixture was acidified with 12N-hydrochloric acid so that 3(4-methylphenyl)isoxazole-5-carboxylic acid precipitated as crystals. The crystals were collected by filtration and then dried. Analytical results of the crystals obtained: Yield: 7.3 g (97.5%). Melting point: 209°–211° C.

(3) 3-(4-Methylphenyl)isoxazole-5-carboxylic acid chloride

Using 40 ml of thionyl chloride, 7.3 g (35.9 mmol) of 3-(4-methylphenyl)isoxazole-5-carboxylic acid obtained above in the procedure (2) were refluxed for 4 hours in the presence of 0.1 ml of dimethylformamide. Thionyl chloride was distilled off under reduced pressure, followed by the addition of 100 ml of benzene. The resultant mixture was distilled under reduced pressure so that 3-(4-methylphenyl)isoxazole-5-carboxylic acid chloride was obtained as a solid. The solid was provided for the next step without purification.

(4) 3-(4-Methylphenyl)-5-butyrylisoxazole

In 50 ml of benzene, 2.6 g (57.5 mmol) of 60% sodium hydride were added to dipyranyl ethylmalonate which had been prepared from 5.7 g (43.2 mmol) of ethylmalonic acid, 9.0 g (107.1 mmol) of 3,4-dihydropyran and 1 droplet of concentrated sulfuric acid. At 40°–50° C., the ethylmalonate was converted to sodium dipyranyl malonate, to which a tetrahydrofuran solution of 3-(4-methylphenyl)isoxazole-5-carboxylic acid chloride synthesized above in the procedure (3) was added dropwise at room temperature. They were reacted for 3 hours. The reaction mixture was added with 10 ml of acetic acid and then heated under reflux for 6 hours. The mixture thus obtained was added into water and then extracted with benzene. The benzene extract was washed successively with an aqueous solution of sodium hydrogencarbonate and water. The organic layer was dried over anhydrous sodium sulfate and the solvent was distilled off. Hexane was added to the residue, and 3-(4-methylphenyl)-5-butyrylisoxazole precipitated as crystals was collected by filtration. Analytical results of the crystals obtained: Yield: 6.3 g (76.5%). Melting point: 86°–87° C.

(5)
3-(4-Methylphenyl)-5-{2-(1-pyrrolidinylmethyl)-butyryl}-isoxazole hydrochloride In 2 ml of dioxane, 2.0 g (8.7 mmol) of the ketone derivative [3-(4 -methylphenyl ) -5-butyrylisoxazole] prepared above in the procedure (4) was heated under reflux for 1 hour along with 0.94 g (8.8 mmol) of pyrrolidine hydrochloride, 0.28 g (9.3 mmol) of paraformaldehyde and two droplets of 12N-hydrochloric acid. Since a white solid was then precipitated upon addition of ethyl ether, the solid was collected by filtration and washed with ethyl ether. The solid was dissolved in water. The resulting solution was alkalinized with sodium carbonate and then extracted with ethyl ether. The solvent was distilled off, whereby the title compound, i.e., the aminoketone derivative [3-(4-methylphenyl)-5-{2-(1pyrrolidinylmethyl)butyryl}isoxazole] was obtained as crystals. Analytical results of the crystals obtained: Yield: 1.2 g (44.0%). Melting point: 79°–81° C.

NMR (δ ppm,CDCl$_3$): 0.8–1.1(3H,m). 1.3–2.1(6H,m), 2.3(3H,s), 2.2–3.8(7H,m), 7.1(1H,s), 7.1–7.3(2H,m), 7.6–7.8(2H,m).

In a manner similar to Example 22, the aminoketone derivative was converted with a 4N-hydrochloric acid-dioxane solution to its hydrochloride in ethyl acetate. Analytical results of the hydrochloride obtained: Melting point: 158°–160° C. Elemental analysis data: Shown in Table 5.

EXAMPLES 37–41

The respective compounds shown in Table 5 were obtained in a similar manner to Example 36 except that the R$^6$-introducing benzaldoxime derivatives (74.1 mmol) shown in Table 5 were employed in place of 4-methylbenzaldoxime used in Example 36-(1).

EXAMPLE 46

3-Phenyl-5-{2-(1-pyrrolidinylmethyl)-3-methyl-butyryl}-isoxazole hydrochloride (1) 3-Phenylisoxazole-5-aldehyde Dissolved in 500 ml of dichloromethane were 29 g (165.7 mmol) of 3-phenyl-5-hydroxymethylisoxazole prepared in Example 28 and 80 g of "Florisil" (trade mark), followed by the addition of 74 g (342.6 mmol) of pyridinium chlorochromate. They were reacted for 7 hours at room temperature. After an insoluble material was filtered off, the filtrate was added into water and then extracted with dichloromethane. After the solvent was distilled off, the residue was purified by silica gel chromatography (eluent: chloroform) so that 3-phenylisoxazole-5-aldehyde was obtained as crystals. Analytical results of the crystals obtained: Yield: 26.0 g (90.7%). Melting point: 67°–69° C.

(2) 3-Phenyl-5-(3-methylbutyryl)isoxazole

To a solution of 5.0 g (28.9 mmol) of the aldehyde derivative (3-phenylisoxazole-5-aldehyde), which had been prepared above in the procedure (1), in 40 ml of tetrahydrofuran, was added dropwise at −50° C. to −30° C. a solution of isobutylmagnesium bromide, which had been prepared from 1.4 g of metallic magne-

TABLE 5

| Ex. | R$^6$ | Molecular formula | Melting point (°C.) | Elemental analysis data (%) Calculated (upper) Found (lower) | | | | |
|---|---|---|---|---|---|---|---|---|
| 36 | 4-CH$_3$-C$_6$H$_4$- | C$_{19}$H$_{24}$N$_2$O$_2$.HCl | 158–160 | C 65.41 64.50 | H 7.22 6.73 | N 8.03 8.02 | Cl 10.16 10.05 | |
| 37 | 4-CF$_3$-C$_6$H$_4$- | C$_{19}$H$_{21}$F$_3$N$_2$O$_2$.HCl | 163–164 | C 56.64 56.13 | H 5.51 5.25 | N 6.96 6.95 | F 14.15 13.62 | Cl 8.80 9.03 |
| 38 | 5-methyl-2-furyl | C$_{17}$H$_{22}$N$_2$O$_3$.HCl | 139–141 | C 60.26 59.83 | H 6.84 6.53 | N 8.27 8.34 | Cl 10.46 10.41 | |
| 39 | 2-CH$_3$-C$_6$H$_4$- | C$_{19}$H$_{24}$N$_2$O$_2$.HCl | 151–153 | C 65.41 64.63 | H 7.22 7.23 | N 8.03 7.96 | Cl 10.16 10.30 | |
| 40 | 4-F-C$_6$H$_4$- | C$_{18}$H$_{21}$FN$_2$O$_2$.HCl | 161–162 | C 61.27 61.17 | H 6.28 6.31 | N 7.94 7.15 | Cl 10.05 9.74 | F 5.38 5.14 |
| 41 | 3-NHSO$_2$CH$_3$-C$_6$H$_4$- | C$_{19}$H$_{25}$N$_3$SO$_4$.HCl | 153–154 | C 53.33 52.96 | H 6.12 5.98 | N 9.82 9.84 | Cl 8.28 8.26 | |

EXAMPLES 42–45

The respective compounds shown in Table 6 were obtained in a similar manner to Example 28 except that butylmalonic acid, benzylmalonic acid, methoxyethyl-malonic acid and cyclopropylmalonic acid (each, 43.2 mmol) were used, respectively instead of ethymalonic acid employed in Example 28-(4). The analytical results of the individual compounds thus obtained are shown in Table 6.

sium and 7.9 g (57.7 mmol) of isobutyl bromide, in 80 ml of tetrahydrofuran. After completion of the dropwise addition, they were reacted for 1 hour at the same temperature. Thereafter, a saturated aqueous solution of ammonium chloride was added. The reaction mixture was added into water and then extracted with diethyl ether. The solvent was distilled off. An oily residue thus obtained was dissolved in 50 ml of acetone, followed by the oxidation with the Jones' reagent under ice cooling. Isopropyl alcohol was added to react the same with the Jones' reagent, and an insoluble material was then filtered off. After substantial removal of acetone by distillation, the residue was added into water and then extracted with ethyl acetate. Subsequent removal of the solvent by distillation, the residue was purified by silica gel chromatography (eluent: chloroform) so that 3-phenyl-5-(3-methyl-butyryl) isoxazole was obtained as crystals. Analytical results of the crystals obtained: Yield: 1.5 g (22.7%). Melting point: 62°–64° C.

3-Phenyl-5-{2-(1-pyrrolidinylmethyl)-3-methyl-butyryl}-isoxazole hydrochloride

From 1.5 g (6.6 mmol) of 3-phenyl-5-(3-methyl-butyryl)isoxazole prepared above in the procedure (2), 0.84 g (7.9 mmol) of piperidine hydrochloride, and 0.26 g (8.7 mmol) of paraformaldehyde, the free base of 3-phenyl-5-{2-(1-pyrrolidinylmethyl)-3-methyl-butyryl}-isoxazole was obtained as crystals in a manner similar to Example 28. Analytical results of the crystals obtained: Yield: 0.7 g (34.3%). Melting point: 77°–79° C.

NMR (δ ppm,CDCl$_3$): 0.9–1.1(6H,m), 1.2–2.8(10H,m), 3.0–3.6(2H,m), 7.2(1H,s), 7.3–7.8(3H,m), 7.6–8.0(2H,m).

The free base (6.7 g) was dissolved in 20 ml of ethyl acetate, followed by the addition of 2 ml of a 4N-hydrochloric acid-dioxane solution. The resultant mixture was concentrated, so that 3-phenyl-5-{2-(1-pyrrolidinylmethyl)-3-methylbutyryl}isoxazole hydrochloride was obtained as crystals. Analytical results of the crystals obtained: Yield: 0.6 g (76.7%). Melting point: 167°–168° C. Elemental analysis data: Shown in Table 6.

EXAMPLES 47–49

The respective compounds shown in Table 6 were obtained in a similar manner to Example 46 except that n-butyl bromide, 1-bromo-3-butene and 1-bromo-2-trifluoromethylethane (each, 57.7 mmol) were used, respectively instead of isobutyl bromide employed in Example 46-(2). The analytical results of the individual compounds thus obtained are shown in Table 6.

EXAMPLE 50

3-Phenyl-5-{2-methoxy-3-(1-pyrrolidinyl)propionyl}-isoxazole hydrochloride (1) 3-Phenyl-5-(α-trimethylsilyloxyvinyl)isoxazole Added to 50 ml of acetonitrile were 5.8 g (31.0 mmol) of 3-phenyl-5-acetylisoxazole and 4.7 g (46.5 mmol) of triethylamine, followed by the dropwise addition of 8.7 g (43.5 g mmol) of trimethylsilane iodide at room temperature. After they were reacted for 24 hours, the reaction mixture was added into ice water and then extracted with n-hexane. The title compound was obtained as oil. Analytical results of the crystals obtained: Yield: 6.5 g (80.9%).

NMR (δ ppm, CDCl$_3$): 0.2(9H,s), 4.8(1H,m), 5.2(1H,m), 6.7(1H,m), 7.3–7.6(3H,m), 7.6–8.0(2H,m).

(2) 3-Phenyl-5-(2-methoxyacetyl)isoxazole

To 120 ml of methyl alcohol, 7.5 g (34.1 mmol) of iodosobenzene and 8.8 g (62.0 mmol) of boron trifluoride etherate were added. The resulting solution was cooled to −70° C., followed by the addition of the vinyl derivative prepared above in the procedure (1). After they were reacted for 1 hour at the same temperature, the internal temperature was returned to room temperature. The reaction was allowed to proceed for further 30 minutes at room temperature. Methyl alcohol was distilled off under reduced pressure, followed by the addition of 100 ml of water and the further addition of a 5% aqueous solution of sodium hydrogencarbonate. The mixture thus prepared was extracted with ethyl ether. After the solvent was distilled off, the residue was purified by silica gel chromatography (eluent: 20:1 n-hexane/ethyl acetate) so that the title compound was obtained as oil. Analytical results of the crystals obtained: Yield: 2.0 g (36.7%).

NMR (δ ppm,CDCl$_3$): 3.5(3H,s). 4.6(2H,s), 7.2(1H,s), 7.2–7.6(3H,m), 7.6–8.0(2H,m).

(3) 3-Phenyl-5-{2-methoxy-3-(1-pyrrolidinyl)propionyl}-isoxazole hydrochloride

Added to 2.0 g (9.2 mmol) of 3-phenyl-5-(2-methoxyacetyl)isoxazole prepared above in the procedure (2) were 1.2 g (11.2 mmol) of pyrrolidine hydrochloride, 0.33 g (11.0 mmol) of paraformaldehyde, 3 ml of dioxane and 2 droplets of 12N-hydrochloric acid. They were reacted under reflux for 30 minutes. After completion of the reaction, water and ethyl ether were added. A water layer thus formed was isolated and then alkalinized with an aqueous solution of sodium carbonate. The resultant mixture was extracted with ethyl ether. The organic layer was collected and concentrated, so that a Mannich base as the title compound was obtained as oil. Analytical results of the crystals obtained: Yield: 0.32 g (11.5%).

NMR (δ ppm,CDCl$_3$): 1.5–2.0(4H,m) , 2.5–2.9(4H,m), 3.0–3.2(2H,m), 3.5(3H,s), 4.6(1H,t,J=5 Hz) , 7.2(1H,s), 7.2–7.6(3H,m), 7.7–8.0(2H,m).

The above oil was dissolved in ethyl acetate and then converted with a 4N-hydrochloric acid-dioxane solution to its hydrochloride. Its physical data and elemental analysis data are shown in Table 6.

TABLE 6

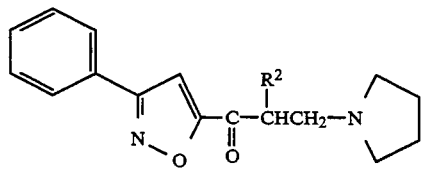

| Ex. | $R^2$ | Molecular formula | Melting point (°C.) | Elemental analysis data (%) Calculated (upper) Found (lower) | | | |
|---|---|---|---|---|---|---|---|
| | | | | C | H | N | Cl |
| 42 | $-CH_2CH_2CH_2CH_3$ | $C_{20}H_{26}N_2O_2 \cdot HCl$ | 166–167 | 66.20 | 7.72 | 7.72 | 9.77 |
| | | | | 65.38 | 7.47 | 7.79 | 9.84 |
| 43 | $-CH_2-\langle\bigcirc\rangle$ | $C_{21}H_{24}N_2O_2 \cdot HCl$ | 166–168 | 67.64 | 6.75 | 7.51 | 9.51 |
| | | | | 69.27 | 6.22 | 7.05 | 9.24 |
| 44 | $-CH_2CH_2OCH_3$ | $C_{19}H_{24}N_2O_3 \cdot HCl$ | 150–152 | 62.55 | 6.91 | 7.68 | 9.72 |
| | | | | 61.53 | 6.91 | 7.68 | 10.20 |
| 45 | $-CH_2-\triangleleft$ | $C_{20}H_{24}N_2O_2 \cdot HCl$ | 186–187 | 66.57 | 6.98 | 7.76 | 9.82 |
| | | | | 66.36 | 6.89 | 7.74 | 9.80 |
| 46 | $-\underset{CH_3}{\overset{\mid}{CHCH_3}}$ | $C_{19}H_{24}N_2O_2 \cdot HCl$ | 167–168 | 65.41 | 7.22 | 8.03 | 10.16 |
| | | | | 64.76 | 7.03 | 7.86 | 10.71 |
| 47 | $-CH_2CH_2CH_3$ | $C_{19}H_{24}N_2O_2 \cdot HCl$ | 156–158 | 65.41 | 7.22 | 8.03 | 10.16 |
| | | | | 65.03 | 7.05 | 8.02 | 10.61 |
| 48 | $-CH_2CH=CH_2$ | $C_{19}H_{22}N_2O_2 \cdot HCl$ | 168–170 | 65.79 | 6.63 | 8.08 | 10.22 |
| | | | | 65.39 | 6.67 | 8.10 | 10.65 |
| 49 | $-CH_2CF_3$ | $C_{18}H_{19}F_3N_2O_2 \cdot HCl$ | 128–129 | C | H | N F | Cl |
| | | | | 55.60 | 5.18 | 7.20 14.66 | 9.12 |
| | | | | 55.37 | 5.09 | 7.15 14.39 | 9.26 |
| 50 | $-OCH_3$ | $C_{17}H_{20}N_2O_3 \cdot HCl$ | 135–137 | 60.62 | 6.28 | 8.32 | 10.59 |
| | | | | 59.99 | 6.38 | 8.12 | 10.95 |

EXAMPLE 51

3-(2-methyl-3-piperidinopropionyl)-5-phenylisoxazole hydrochloride (1) Ethyl benzoylpiruvate Dissolved in 80 ml of dry ethyl alcohol were 12 g (0.3 mol) of 60% sodium hydride, to which a liquid mixture consisting of 36 g (0.3 mol) of acetophenone and 44 g (0.3 mol) of diethyl oxalate was added dropwise under ice cooling (internal temperature: 8°–10° C.). After completion of the dropwise addition, the reaction mixture was stirred for 2 hours at room temperature and then allowed to stand overnight. Added further was n-hexane. A precipitate was collected by filtration and then dissolved in water. Acetic acid was added to the aqueous solution, so that the solution was acidified weakly. The solution was then extracted with ethyl acetate. The solvent was distilled off and the residue was left over in a cool place. Crystals formed were collected by filtration and dried, whereby ethyl benzoylpiruvate was obtained as colorless crystals. Analytical results of the crystals obtained: Yield: 54 g (82%).
Melting point: 37.5°–39° C.

(2) 3-Ethoxycarbonyl-5-phenylisoxazole

In accordance with a known process [J. Heterocyclic Chem., 19, 557 (1982)], the title compound was prepared in the following manner.

Added to 600 ml of ethyl alcohol were 54 g (0.245 mol) of ethyl benzoylpiruvate prepared above in the procedure (1) and 60 g (0.84 mol) of hydroxylamine hydrochloride. After they were heated under reflux for 3 hours, the solvent was distilled off so that the reaction mixture was concentrated to about half. The concentrate was added to 300 ml of water. A precipitate was collected by filtration and dissolved in ethyl acetate. The resulting ethyl acetate was washed with a dilute aqueous solution of sodium hydrogencarbonate.

The organic layer was dried over anhydrous magnesium sulfate. The solvent was then distilled off. Chilled n-hexane was added to crystals solidified. The crystals were collected by filtration, so that 3-ethoxycarbonyl-5-phenylisoxazole was obtained as colorless crystals. Analytical results of the crystals obtained: Yield: 43.5 g (82%). Melting point: 48°–49.5° C.

(3) 3-Propionyl-5-phenylisoxazole

In accordance with a known process [Synthesis, 877 (1984)], the title compound was prepared in the following manner.

To 20 ml of a toluene solution containing 28.8 g (0.4 mol) of tetrahydrofuran, 4.8 g (0.2 mol) of magnesium and a catalytic amount of iodine, a solution of 24 g (0.22 mol) of ethyl bromide in 70 ml of toluene was added dropwise in a temperature range of 20°-30° C. The resultant mixture was stirred for 2 hours under the same conditions, followed by the addition of 60.8 g (0.6 mol) of triethylamine. In addition, a solution of 21.6 g (0.1 mol) of the ester derivative prepared above in the procedure (2), i.e., (3-ethoxycarbonyl-5-phenylisoxazole) in 200 ml of toluene was added dropwise over 1 hour while the temperature was maintained in a range of 5°-10° C. After the resultant mixture was stirred for 2 hours at the same temperature, the reaction mixture was added with 140 ml of 4N-hydrochloric acid. The organic layer was washed successively with water, a 5% aqueous solution of sodium hydrogencarbonate and water. The organic layer was distilled under reduced pressure. The residue was dissolved in 400 ml of methanol, followed by the addition of 6 ml of a 20% aqueous solution of potassium hydroxide. They were reacted at 40° C for 30 minutes. After completion of the reaction, 12N-hydrochloric acid was added to control the pH to 2. Under reduced pressure, methanol was distilled off. The residue was added with toluene and water. The organic layer was washed successively with a 5% aqueous solution of sodium hydrogencarbonate and water and dried over anhydrous magnesium sulfate. The solvent was then distilled off, whereby a crude oily matter was obtained. The oily matter was purified by silica gel chromatography, so that 3-propionyl-5-phenylisoxazole was obtained as colorless crystals. Analytical results of the crystals obtained: Yield: 8 g (40%). Melting point: 88°-89° C. (88° C. in literature).

(4)
3-(2-methyl-3-piperidinopropionyl)-5-phenylisoxazole hydrochloride

To a mixture consisting of 1.5 g (7.5 mmol) of the ketone derivative, i.e., (3-propionyl-5-phenylisoxazole) prepared above in the procedure (3), 0.99 g (8.2 mmol) of piperidine hydrochloride, 0.36 g of paraformaldehyde and 3 ml of dioxane, 0.03 ml of 12N-hydrochloric acid was added. The resultant mixture was heated under reflux for 2 hours. After completion of the reaction, ethyl ether was added. Colorless crystals thus formed were collected by filtration and added to a saturated aqueous solution of sodium hydrogencarbonate. The solution was extracted with ethyl ether. The solvent was distilled off so that 3-(2-methyl-3-piperidinopropionyl)-5-phenylisoxazole was obtained as colorless crystals. Analytical results of the crystals obtained: Yield: 1.2 g (48.1%). Melting point: 87°-89° C.

NMR (δppm,CDCl₃): 1.2(3H,d,J=7Hz), 1.1–1.7(6H,m), 2.0–3.1(6H,m), 3.9(1H,m) 6.9(1H,m), 7.5–8.0 (5H, m).

Those crystals were dissolved in ethyl ether, into which hydrochloric acid gas was introduced under ice cooling. A white solid thus precipitated was collected by filtration and then dried, so that the hydrochloride was obtained.

The analytical results of the hydrochloride thus obtained are shown in Table 7.

EXAMPLE 52

The compound shown in Table 7 was obtained in a similar manner to Example 51 except that propyl bromide was used in place of ethyl bromide employed in Example 51-(3) and pyrrolidine hydrochloride (8.2 mmol) was used in lieu of piperidine hydrochloride employed in Example 51-(4). Its analytical results are shown in Table 7.

TABLE 7

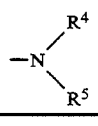

| Ex. | R² | —N(R⁴)(R⁵) | Molecular formula | Melting point (°C.) | Elemental analysis data (%) Calculated (upper) Found (lower) | | | |
|---|---|---|---|---|---|---|---|---|
| | | | | | C | H | N | Cl |
| 51 | —CH₃ | 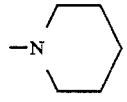 | C₁₈H₂₂N₂O₂.HCl | 161–162 | 64.57 | 6.92 | 8.37 | 10.59 |
| | | | | | 63.80 | 6.94 | 8.21 | 11.01 |
| 52 | —CH₂CH₃ | 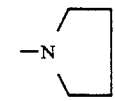 | C₁₈H₂₂N₂O₂.HCl | 162–163 | 64.57 | 6.92 | 8.37 | 10.59 |
| | | | | | 63.82 | 6.71 | 8.38 | 10.80 |

EXAMPLE 53

3-Phenyl-5-{3- (1 -pyrrolidinyl) butyrl}isoxazole hydrochloride (1) 3-Phenyl-5-(2-butenoyl)isoxazole Added to 60 ml of ethyl acetate were 3.03 g (14.1 mmol) of 3-phenyl-5-butyrylisoxazole prepared above in Example 28-(4), 3.24 g (16.9 mmol) of phenylselenyl chloride and 2 droplets of concentrated hydrochloric acid. The resultant mixture was stirred at room temperature for 36 hours. The reaction mixture was concentrated under reduced pressure, followed by the addition of 20 ml of methanol and 60 ml of tetrahydrofuran. While the resultant mixture was stirred at room temperature, 6.03 g (28.2 mmol) of sodium periodate were dissolved.

A mixed solvent which consisted of 20 ml of methanol, 20 ml of tetrahydrofuran and 9 ml of water was added dropwise. After the resultant mixture was stirred at room temperature for 1 hour, the solvent was distilled off. Water and ethyl acetate were added, whereby the reaction product was extracted in an organic layer. The organic layer was collected and dried over anhydrous magnesium sulfate. The solvent was thereafter distilled off. The residue was purified by silica gel chromatography (eluent: 10:1 n-hexane/ethyl acetate) so that 3-phenyl-5-(2-butenoyl)-isoxazole was obtained as colorless crystals. Analytical results of the crystals obtained: Yield: 1.1 g (37%). Melting point: 105°–106° C.

(2) 3-Phenyl-5-{3- (1-pyrrolidinyl) butyryl}isoxazole

Pyrrolidine (5 ml) was added to 1.1 g (5.2-mmol) of 3-phenyl-5-(2-butenoyl)isoxazole prepared above in the procedure (1). The resulting mixture was stirred at room temperature for 3 hours. Water and ethyl acetate were added to the reaction mixture, so that a product formed was extracted in an organic layer. The organic layer was collected, dried over anhydrous magnesium sulfate, and then concentrated, whereby 3-phenyl-5-{3- (1-pyrrolidinyl)butyryl}isoxazole was obtained as colorless oil. Analytical results of the crystals obtained: Yield: 1.35 g (92%).

NMR (δppm,CDCl$_3$): 1.20(3H,d,J=6.2 Hz), 1.40–2.18(4H,m), 2.40–3.73(7H,m), 7.17(1H,s), 7.28–7.62(3H,m), 7.65–8.00(2H,m).

The above oil was dissolved in ethyl acetate, followed by the addition of 4N-hydrochloric aciddioxane solution. The resulting hydrochloride was collected by filtration so that 3-phenyl-5-{3-(1-pyrrolidinyl)butyryl-}isoxazole hydrochloride was obtained.

Its analytical results are shown in Table 8.

EXAMPLE 54

3-Phenyl-5- {2-methyl-3- (1-pyrrolidinyl)butyryl}- isoxazole hydrochloride (1)
3-Phenyl-5-(1-hydroxy-2-methyl-2-butenyl)isoxazole To a solution of 5.0 g (28.9 mmol) of 3-phenyl-isoxazole-5-aldehyde in 40 ml of tetrahydrofuran, was added dropwise at −30° C. a solution of 1.5 g of metallic magnesium and 10.1 g (74.8 mmol) of 2-bromo-2-butene in 80 ml of tetrahydrofuran. After they were reacted at the same temperature for 30 minutes, the temperature of the reaction mixture was allowed to rise to room temperature and a saturated aqueous solution of ammonium chloride was added to terminate the reaction. Water was added, followed by extraction with ethyl ether. The organic layer was successively washed with water and saturated saline and then dried over anhydrous sodium sulfate. After ethyl ether was distilled off, the residue was purified by chromatography on a silica gel column (eluent: 9:1 hexane/ethyl acetate) so that 3-phenyl-5-(1-hydroxy-2-methyl-2-butenyl)isoxazole was obtained as oil.

Its yield was 5.4 g (78.6%).

(2) 3-Phenyl-5-(2-methyl-2-butenoyl)isoxazole

Dissolved in 100 ml of benzene were 5.4 g (23.6 mmol) of 3-phenyl-5-(1-hydroxy-2-methyl-2-butenyl)isoxazole, followed by the addition of 21.0 g (0.24 mol) of manganese dioxide. The mixture was stirred at room temperature for 24 hours. An insoluble material was filtered off and the solvent was distilled off under reduced pressure. The residue was purified by silica gel chromatography (eluent: 30:1 n-hexane/ethyl acetate), whereby 3-phenyl-5-(2-methyl-2butenoyl)isoxazole was obtained as colorless oil. Analytical results of the crystals obtained: Yield: 3.6 g (67%).

NMR (δppm,CDCl$_3$): 1.66(3H,dq,J=7.42,1.48 Hz), 2.01(3H,quintet, J=1.48 Hz), 5.99(1H,qq,J=7.42,1.48 Hz), 7.13 (1H,s) , 7.32–7.42 (3H,m) , 7.68–7.78 (2H,m).

(3) 3-Phenyl-5- {2-methyl-3-(1-pyrrolidinyl)butyryl} isoxazole

In a similar manner to Example 53, 3-phenyl-5-(2-methyl-3-pyrrolidino) butyrylisoxazole was obtained as yellow oil from 3.6 g (15.9 mmol) of 3-phenyl-5-(2-methyl-2-butenoyl)isoxazole obtained above in the procedure (2) and 1.1 g (15.9 mmol) of pyrrolidine. Yield: 1.32 g (28%).

The above oil was dissolved in ethyl acetate, followed by the addition of a 4N-hydrochloric acid-dioxane solution. Its hydrochloride thus formed was collected by filtration, whereby 3-phenyl-5-{2-methyl-3-(1-pyrrolidinyl) butyryl}isoxazole hydrochloride was obtained.

Its analytical results are shown in Table 8.

EXAMPLE 55

3-Phenyl-5- {2-(1-pyrrolidinyl)cyclohexanoyl} isoxazole hydrochloride (1) 3-phenyl-5-(1-cyclohexenoyl)isoxazole To 30 ml of thionyl chloride, 3.1 g (16.4 mmol) of 3-phenylisoxazole-5-carboxylic acid were added. The resultant mixture was refluxed for 1 hour and then concentrated, whereby the acid chloride having a pale yellow color was obtained. To 50 ml of chloroform, 2.48 g (16.4 mmol) of 1-(1-pyrrolidinyl)-1-cyclohexene and 1.7 g (16.4 mmol) of triethylamine were added. Under ice cooling, a chloroform solution of the acid chloride prepared above was added dropwise. After the dropwise addition, the resultant mixture was stirred at room temperature for 2 hours. The solvent was distilled off under reduced pressure, followed by the addition of 70 ml of methanol. While the solution thus formed was stirred at room temperature, 0.8 g (13.1 mmol) of sodium cyanoborohydride and a 10% hydrochloric acid-methanol solution were added to acidify the solution. After the solution was stirred for 2 hours, water and dichloromethane were added, so that the reaction product was extracted into an organic layer. The organic layer was collected, dried over anhydrous magnesium sulfate, and then concentrated to dryness. The residue was purified by silica gel chromatography (eluent: 10:1 n-hexane/ethyl acetate), Whereby 3-phenyl-5-(1-cyclohexenoyl)isoxazole was obtained as colorless crystals. Analytical results of the crystals obtained: Yield: 0.98 g (24%). Melting point: 70°–71° C.

(2) 3-Phenyl-5- {2-(1-pyrrolidinyl)cyclohexanoyl} isoxazole

Pyrrolidine (5 ml) was added to 0.98 g (3.9 mmol) of 3-phenyl-5-(1-cyclohexenoyl)isoxazole prepared above in the procedure (1). The resultant mixture was stirred at room temperature for 1 hour and then concentrated under reduced pressure. To the concentrate was added diethyl ether and then 10% hydrochloric acid, whereby the reaction product was extracted in a water layer. The water layer was collected, alkalinized with a 10% aqueous solution of sodium hydroxide, and then extracted with dichloromethane. methane. The solvent was distilled off, so that 3-phenyl-5-{2-(1-pyrrolidinyl)cyclohexanoyl} isoxazole was obtained as yellow crystals. Analytical results of the crystals obtained: Yield: 0.44 g (35%). Melting point: 109°–111° C.

NMR (δppm, CDCl$_3$): 1.20–2.20(12H,m), 2.38–2.59(2H,m), 2.60–2.85(2H,m), 3.17(1H,dt,J=3.2, 11.3 Hz), 3.45(1H,dt,J=3.5,11.3 Hz), 7.17 (1H,s), 7.35–7.56(3H,m), 7.74–7.90(2H,m).

The above crystals were dissolved in ethyl acetate and then treated in a similar manner to Example 53, whereby 3-phenyl-5- {2- (1-pyrrolidinyl)cyclohexanoyl}-isoxazole hydrochloride was obtained.

Its analytical results are shown in Table 8.

EXAMPLE 56

The compound shown in Table 8 was obtained in a similar manner to Example 55 except that 1-(1-pyrrolidinyl)-1-cyclopentene (16.4 mmol) was employed in lieu of 1-(1-pyrrolidinyl)-1-cyclohexene used in Example 55-(1). Its analytical results are shown in Table 8.

EXAMPLE 57

The compound shown in Table 8 was obtained in a similar manner to Example 55 except that 2,1-benzisothiazole-3-carboxylic acid (16.4 mmol) was employed in place of 3-phenylisoxazole-5-carboxylic acid used in Example 55-(1).

Its analytical results are shown in Table 8.

EXAMPLE 58

3- {2- (1-pyrrolidinylmethyl) butyryl}-1,2-benzisoxazole hydrochloride (1) 3-Butyryl-1,2-benzisoxazole Using 3.7 g (23 retool) of 3-carboxy-1,2-benzisoxazole prepared in accordance with a known process [J. Amer. Chem. Soc., 97, 7305 (1975)], 3.34 g (25 mmol) of ethylmalonic acid and 6.4 g of 3,4-dihydropyran, 3-butyryl-1,2-benzisoxazole was obtained as colorless crystals by similar treatment to Example 28-(4). Analytical results of the crystals obtained: Yield: 3.5 g (85%). Melting point: 33°–35° C.

IR (γKBR, cm$^{-1}$): 2950, 1700, 1480, 900, 760.

(2) 3-{2-(1-pyrrolidinylmethyl)butyryl}-1,2-benzisoxazole hydrochloride

Added to 10 ml of ethanol were 1.55 g (8.2 mmol) of 3-butyryl-1,2-benzisoxazole prepared above in the procedure (1), 0.52 ml (9.9 mmol) of a 37% aqueous solution of formaldehyde and 0.82 ml (9.8 mmol) of pyrrolidine. The resultant mixture was heated under reflux for 3 hours. After cooling, the solvent was distilled off. The residue thus obtained was added to 50 ml of ethyl acetate, followed by extraction with 50 ml of dilute hydrochloric acid. A water layer thus obtained was alkalinized with an aqueous solution of sodium hydrogencarbonate, followed by extraction with 50 ml of ethyl acetate. The organic layer was dried over anhydrous magnesium sulfate and the solvent was then distilled off, whereby 3-{2-(1-pyrrolidinylmethyl)-butyryl}-1,2-ben-

TABLE 8

$$R^9-\overset{O}{\underset{\|}{C}}-R^{10}-N\diagdown$$

| Ex. | R$^9$ | R$^{10}$ | Molecular formula | Melting point (°C.) | Elemental analysis data (%) Calculated (upper) Found (lower) | | | |
|-----|-------|----------|-------------------|---------------------|---|---|---|---|
| | | | | | C | H | N | Cl |
| 53 | (3-phenylisoxazol-5-yl) | —CH$_2$—CH—<br>         \|<br>         CH$_3$ | C$_{17}$H$_{20}$N$_2$O$_2$.HCl | 113–115 | 58.99<br>58.13 | 6.67<br>7.05 | 8.09<br>8.32 | 13.31<br>13.68 |
| 54 | ″ | —CH—CH—<br>\|       \|<br>CH$_3$  CH$_3$ | C$_{18}$H$_{22}$N$_2$O$_2$.HCl | 57–60 | 62.88<br>62.38 | 7.03<br>7.32 | 8.15<br>7.97 | 10.31<br>10.85 |
| 55 | ″ | (cyclohexyl) | C$_{20}$H$_{24}$N$_2$O$_2$.HCl | 134–135 | 65.90<br>65.39 | 6.94<br>7.11 | 7.68<br>7.78 | 10.70<br>10.32 |
| 56 | ″ | (cyclopentyl) | C$_{19}$H$_{22}$N$_2$O$_2$.HCl | 121–122 | 65.79<br>65.91 | 6.68<br>6.26 | 8.08<br>8.04 | 10.22<br>10.15 |
| 57 | (2,1-benzisothiazol-3-yl) | (cyclohexyl) | C$_{18}$H$_{22}$N$_2$SO.HCl | 153–154 | 60.36<br>59.60 | 6.53<br>6.58 | 7.82<br>8.00 | 11.88<br>11.37 | zisoxazole was obtained as oil. Analytical results of the crystals obtained: Yield: 1.65 g (74%).

NMR (δppm, CDCl₃): 0.95(3H,t,J=7 Hz), 1.50–1.96(6H,m), 2.40–2.45(2H,m), 2.52–2.60(3H,m), 3.14(1H,q,J=10 Hz), 3.86–3.96(1H,m), 7.38–7.45(1H,m), 7.56–7.66(2H,m), 7.25(1H,d,J=8 Hz).

In 60 ml of acetic acid, 1.65 g (6.1 mmol) of the above oil was dissolved. A 4N-hydrochloric acid-dioxane solution (10 ml) was added under ice cooling to the resultant solution, so that the solution was acidified. The solvent was distilled off, and 40 ml of ethyl acetate were added to the residue. A precipitate thus formed was collected by filtration so that 3-{2-(1-pyrrolidinyl-methyl)butyryl}-1,2-benzisoxazole hydrochloride was obtained as colorless crystals. Its yield was 1.7 g (91%). Its analytical results are shown in Table 9.

EXAMPLE 59

3-{2-methyl-3-(1-pyrrolidinyl)propionyl}-2,1-benzisoxazole hydrochloride (1) 2,1-Benzisoxazole-3-carboxylic acid Following a known process [J. Chem. Soc., (C), 2660 (1970)], the title compound was prepared in the following manner.

To 1 l of concentrated sulfuric acid, 40 g (0.22 mol) of orthonitrophenylacetic acid were added, followed by stirring at 105°–110° C. for 90 minutes. After cooling, 2.5 l of ice water in limited amounts was added to the reaction mixture. The resultant mixture was extracted with 1 l of ethyl ether. The extract was dried over anhydrous sodium sulfate and the solvent was distilled off, so that 18.1 g (yield: 50.2%) of 2,1-benzisoxazole-3-carboxylic acid was obtained as crystals.

(2) 3-Propionyl-2,1-benzoisoxazole

Added to 75 ml of dry benzene were 5.3 g (45 mmol) of methylmalonic acid and 11.4 g (0.135 mmol) of 3,4-dihydropyran, followed by the addition of 1 droplet of concentrated sulfuric acid under stirring over a water bath. After one hour, 6 g of sodium hydroxide were added. After the resultant mixture was stirred for 5 minutes, an insoluble material was filtered off. Then, 1.8 g of 60% sodium hydride was added in small portions to the filtrate. After evolution of hydrogen gas subsided, a solution of the acid chloride, which had been prepared from 6.5 g (0.04 mol) of 2,1-benzisoxazole-3-carboxylic acid prepared above in the procedure (1) and 30 ml of thionyl chloride in benzene, was added dropwise under ice cooling. After the resultant solution was stirred for 2 hours at room temperature, 6 ml of acetic acid were added, followed by heating under reflux for 8 hours. After ice cooling, water was added and the reaction product was extracted with ethyl acetate. The extract was purified by silica gel chromatography (eluent: 30:1 n-hexane/ethyl acetate), so that 3-propionyl-2,1-benzisoxazole was obtained as colorless crystals. Analytical results of the crystals obtained: Yield: 5.6 g (80%). Melting point: 51°–53° C.

(3) 3-{2-methyl-3- (1-pyrrolidinyl) propionyl}-2,1-benzisoxazole hydrochloride

Added to 2 ml of dioxane were 2.0 g (11.4 mmol) of the ketone derivative, i.e., 3-propionyl-2,1-benzisoxazole prepared above in the procedure (2), 1.3 g (12.1 mmol) of pyrrolidine hydrochloride, 0.45 g (15.0 mmol) of paraformaldehyde and 2 droplets of 12N-hydrochloric acid. They were reacted under reflux for 30 minutes. After completion of the reaction, water and ethyl ether were added, and a water layer was collected. The water later was alkalinized with an aqueous solution of sodium carbonate and then extracted with ethyl ether. The extract was dried over anhydrous magnesium sulfate. The solvent was then distilled off so that an oily residue was obtained. The oily residue was dissolved in ethyl acetate, followed by the addition of a 4N-hydrochloric acid-dioxane solution under ice cooling. The mixture thus obtained was concentrated at room temperature under reduced pressure. Precipitated crystals of 3-{2-methyl-3-(1-pyrrolidinyl)-propionyl}-2,1-benzisoxazole hydrochloride thus formed were collected by filtration, so that the title compound was obtained. Its yield was 0.9 g (30.5%).

The analytical results of the thus-obtained hydrochloride are shown in Table 9.

EXAMPLE 60

3-{2-(1-pyrrolidinylmethyl)butyryl}-2,1-benzisoxazole fumarate

A Mannic base was prepared in a similar manner to Example 59 except for the use of ethylmalonic acid in place of methylmalonic acid employed in Example 59-(2). Using a solution of fumaric acid in acetone, 3-{2-(1-pyrrolidinylmethyl)butyryl}-2,1-benzisoxazole fumarate was obtained.

Its yield was.0.28 g (13%).

The analytical results of the fumarate thus obtained are shown in Table 9.

EXAMPLES 61 & 62

The compounds shown in Table 9 were obtained in a similar manner to Examples 58 and 59, respectively, except that 2,1-benzisothiazole-3-carboxylic acid prepared in accordance with a known process [J. Chem. Soc. Perkin I., 2057 (1973)] was employed instead of 2,1-benzisoxazole-3-carboxylic acid. The analytical results of the thus-obtained compounds are shown in Table 9.

EXAMPLE 63

The compound shown in Table 9 was obtained in a similar manner to Example 62 except that 4-acetyl-piperidine was employed in place of the pyrrolidine for the introduction of

The analytical results of the thus-obtained compound are shown in Table 9.

EXAMPLE 64

The compound shown in Table 9 was obtained in a similar manner to Example 62 except that morpholine was employed in place of the pyrrolidine for the introduction of

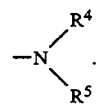

EXAMPLE 65

3-Phenyl-5-{2-methyl-3-(1-pyrrolidinyl)propionyl}-isothiazole hydrochloride (1) 3-Phenyl-5-propionylisothiazole In 30 ml of dry tetrahydrofuran, were dissolved 3.1 g (19.1 mmol) of 3-phenylisothiazole. Under a nitrogen gas stream, the solution was cooled to −78° C. over a dry ice-acetone bath, followed by the dropwise addition of 14.6 ml of n-butyl lithium (1.57 mol/l). After the resultant mixture was stirred for 15 minutes at room temperature, 3.24 g (25 mmol) of propionic anhydride was added. The mixture thus obtained was stirred for 30 minutes, to which a saturated aqueous solution of ammonium chloride and dichloromethane were added at room temperature. The reaction product was thus extracted into an organic layer. The organic layer was collected, dried and then concentrated. The concentrate was purified by silica gel chromatography (eluent: 20:1 n-hexane/ethyl acetate), so that 3-phenyl-5-propionylisothiazole was obtained as colorless oil. Analytical results of the crystals obtained: Yield: 2.12 g (51%).

NMR (δppm,CDCl₃): 1.22(3H,t,J=6.8 Hz), 2.92(2H,q,J=6.8 Hz), 7.17–7.60(3H,m), 7.67–8.07 (2H,m).

3-Phenyl-5-{2-methyl-3-(1-pyrrolidinyl)propionyl}-isothiazole

Added to 20 ml of ethyl alcohol were 2.1 g (9.8 mmol) of 3-phenyl-5-propionylisothiazole prepared above in the procedure (1), 1 ml of a 37% aqueous solution of formaldehyde and 1.6 ml of pyrrolidine, followed by stirring at 60° C. for 1 hour. The solvent was distilled off under reduced pressure. The residue was purified by silica gel chromatography (eluent: 20:1 chloroform/methanol), so that 3-phenyl-5-{2-methyl-3-(1-pyrrolidinyl)propionyl}isothiazole was obtained as yellow oil. Analytical results of the oily matter obtained:

NMR (δppm,CDCl₃): 1.27(3H,d,J=6.6 Hz), 1.3–2.1(4H,m), 2.23–3.10(6H,m), 3.20–3.63(1H,m), 7.27–7.57 (3H,m), 7.8–8.1(2H,m), 7.95(1H,s).

The oil was dissolved in ethyl acetate, followed by the addition of a 4N-hydrochloric acid-dioxane solution. The precipitated hydrochloride was collected by filtration so that 3-phenyl-5-{2-methyl-3-(1-pyrrolidinyl)-propionyl}isothiazole hydrochloride was obtained.

Its analytical results are shown in Table 9.

EXAMPLE 66

3-Phenyl-5-{2-(1-pyrrolidinylmethyl)butyryl}-isothiazole hydrochloride (1) 3-Phenyl-5-(1-hydroxybutyl)isothiazole Dissolved in 60 ml of anhydrous tetrahydrofuran were 3.1 g (19.1 mmol) of 3-phenylisothiazole, followed by the addition 18.2 ml of an n-butyl lithium-hexane solution (1.57 mol/l) under a nitrogen gas stream at −78° C. over a dry ice-acetone bath. After the resulting mixture was stirred for 1 hour, 1.51 g (21 mmol) of butylaldehyde were added dropwise. The solution was stirred for 1 hour at the same temperature, whereby the reaction was completed. Water and chloroform were added. The reaction product was extracted into an organic layer. The organic layer was concentrated and the concentrate was purified by silica gel chromatography (eluent: 20:1 n-hexane/ethyl acetate), so that 3-phenyl-5-(1-hydroxybutyl)isothiazole was obtained as yellow oil.

Its yield was 1.73 g (39%).

(2) 3-Phenyl-5-butyrylisothiazole

To 35 ml of dichloromethane, were added 1.73 g (7.42 mmol) of 3-phenyl-5-(1-hydroxybutyl)isothiazole, 1.1 g (13.4 mmol) of sodium acetate and 2.88 g of Frolisil" (trade mark). While the resultant mixture was vigorously stirred at room temperature, 2.88 g (13.4 mmol) of pyridinium chlorochromate were added at once. After the reaction mixture was stirred for 2 hours, an insoluble material was filtered off and the solvent was then distilled off. The residue was purified by silica gel chromatography (eluent: 20:1 n-hexane/ethyl acetate), whereby 3-phenyl-5-butyrylisothiazole was obtained as colorless crystals.

Its yield was 1.2 g (69%). Melting point: 70°–° C.

(3) 3-Phenyl-5-{2-(1-pyrrolidinylmethyl)butyryl}isothiazole hydrochloride

In a similar manner to Example 62-(2), 1.18 g (5.11 mmol) of 3-phenyl-5-butyrylisothiazole, 0.51 ml of a 37% aqueous solution of formaldehyde and 0.73 g (10.2 mmol) of pyrrolidine were treated in 35 ml of ethyl alcohol. The reaction mixture was similarly treated so that 3-phenyl-5-{2-(1-pyrrolidinylmethyl)-butyryl}isothiazole was obtained as colorless crystals.

Its yield was 1.1 g (61%).

Its analytical data are shown in Table 9.

EXAMPLE 67

3-Methyl-4-{2-methyl-3-(1-pyrrolidinyl)propionyl}-isothiazole hydrochloride (1) 3-Methyl-isothiazole-4-carboxylic acid By a known process (Dutch Patent 6607796; Chemical Abstracts, 67, 100136a), 3-methyl-isothiazole-4-carboxylic acid was obtained as colorless crystals from 20 g (0.174 mol) of methyl β-aminocrotonate, 44 g (0.43 mol) of triethylamine and 20 g (0.174 mol) of thiophosgene. Analytical results of the crystals obtained: Yield: 7.3 g (29%). Melting point: 227°–229° C.

(2) 3-Methyl-4-propionylisothiazole

In a manner similar to Example 58, 3-methyl-4-propionylisothiazole was obtained as colorless crystals from 7.3 g (51 mmol) of 3-methyl-isothiazole-4-carboxylic acid prepared above in the procedure (1), 6.5 g (55 mmol) of methylmalonic acid and 14 g (165 mmol) of 2,3-dihydropyran. Analytical results of the crystals obtained: Melting point: 46°–48° C. IR (γKBr,cm⁻¹): 1670, 1500, 1410, 795

(3) 3-Methyl-4-{2-methyl-3-(1-pyrroidinyl)propionyl}isothiazole hydrochloride

In a manner similar to Example 59-(3), 3-methyl-4-{2-methyl-3-(1-pyrrolidinyl)propionyl}isothiazole hydrochloride was obtained as colorless crystals from 2 g (13 mmol) of the ketone derivative, i.e., 3-methyl-4-propionylisothiazole prepared above in the procedure (2), 0.51 g (17 mmol) of paraformaldehyde and 1.7 g (16 mmol) of pyrrolidine hydrochloride.

Its yield was 1.9 g (53%).

The analytical results of the hydrochloride thus obtained are shown in Table 9.

EXAMPLE 68

3-Phenyl-5-methyl-4-(2-methyl-3-piperidinopropionyl-)isoxazole hydrochloride (1) 3-Phenyl-5-methylisoxazole-4-carboxylic acid Added to 100 ml of ethyl alcohol were 8.5 g (65.4 mmol) of ethyl acetoacetate, to which 2.8 g of 60% sodium hydride were added in small portions to dissolve the same. While the resultant mixture was stirred at room temperature, a solution of 10.0 g (64.5 mmol) of benzenehydroxamoyl chloride in 15 ml of ethyl ether was added dropwise. The mixture was stirred for 24 hours at room temperature and the solvent was distilled off. Water and ethyl ether were added so that the reaction product was extracted into an organic layer. The organic layer was washed with a dilute aqueous solution of sodium hydroxide. The solvent was distilled off, whereby an oily residue was obtained. The oily residue was dissolved in methyl alcohol, followed by the addition of a 10N aqueous solution of sodium hydroxide so that the reaction product was hydrolyzed. Water and ethyl ether were added to the reaction mixture, so that the reaction product was extracted in a water layer. The water layer was collected, to which 12N-hydrochloric acid was added to acidify the same. Crystals precipitated were collected by filtration, washed with water and then dried, whereby 3-phenyl-5-methylisoxazole-4-carboxylic acid was obtained. Analytical results of the crystals obtained: Yield: 5.12 g (39%). Melting point: 189°–190° C.

(2) 3-Phenyl-4-propionyl-5-methylisoxazole

In a similar manner to Example 58, 3-phenyl-4-propionyl-5-methylisoxazole was obtained as colorless oil from the acid chloride, which had been prepared from 5.1 g (25.1 mmol) of 3-phenyl-5-methylisoxazole-5-carboxylic acid, and 3.6 g (30.0 mmol) of methylmalonic acid, 6.4 g (76.2 mmol) of 3,4-dihydropyran and 2 droplets of concentrated sulfuric acid. Analytical results of the crystals obtained: Yield: 3.2 g (59.2%).

NMR (δppm, CDCl$_3$): 1.0(3H,t,J=7 Hz), 2.4(2H,q,J=7 Hz), 2.7 (3H,s), 7.5(5H,s).

3-Phenyl-5-methyl-4-(2-methyl-3-piperidinopropionyl)-isoxazole hydrochloride

Added to 3 ml of dioxane were 2.0 g (9.3 mmol) of 3-phenyl-4-propionyl-5-methylisoxazole prepared above in the procedure (2), 1.4 g (11.6 mmol) of piperidine hydrochloride, 0.4 g (13.3 mmol) of paraformaldehyde and 3 droplets of 12N-hydrochloric acid. The resultant mixture was heated under reflux for 30 minutes. After completion of the reaction, water and ethyl ether were added, followed by separation of a water layer. An aqueous solution of sodium carbonate was added to the water layer to alkalinize the same, followed by extraction with ethyl ether. The organic layer was dried and the solvent was distilled off, whereby a Mannich base, namely, 3-phenyl-5-methyl-4-(2-methyl-3-piperidinopropionyl) isoxazole was obtained as oil. Analytical results were as follows: Yield: 2.1 g (72.4%).

NMR (δppm, CDCl$_3$): 1.0(3H,d,J=6 Hz), 1.1–1.7 (6H,m), 1.9–2.2(5H,m). 2.3–3.2(2H,m), 2.7 (3H,s), 7.2–7.7 (5H,m).

The oil was dissolved in ethyl acetate, followed by the addition of a 4N-hydrochloric acid-dioxane solution. A precipitate was collected so that 3-phenyl-5-methyl-4- (2-methyl-3-piperidinopropionyl) isoxazole hydrochloride was obtained.

Its analytical results are shown in Table 9.

TABLE 9

$$R^1-\overset{\overset{O}{\|}}{C}-\underset{\underset{R^2}{|}}{CH}-CH_2-N\overset{R^4}{\underset{R^5}{\diagdown}}$$

| Ex. | R$^1$ | R$^2$ | $-N\overset{R^4}{\underset{R^5}{\diagdown}}$ | Molecular formula | Melting point (°C.) | Elemental analysis data (%) Calcd (upper) Found (lower) | | | |
|---|---|---|---|---|---|---|---|---|---|
| 58 | (3-phenyl-isoxazole, O-N) | —CH$_2$CH$_3$ | —N(piperidine) | C$_{16}$H$_{20}$N$_2$O$_2$.HCl | 131–133 | C 62.23 62.34 | H 6.85 6.78 | N 9.07 8.98 | Cl 11.48 11.65 |
| 59 | (3-phenyl-isoxazole, N-O) | —CH$_3$ | " | C$_{15}$H$_{18}$N$_2$O$_2$.HCl | 160–161 | C 61.12 60.55 | H 6.50 6.59 | N 9.50 9.48 | Cl 12.03 12.42 |
| 60 | (3-phenyl-isoxazole, N-O) | —CH$_2$CH$_3$ | " | C$_{16}$H$_{20}$N$_2$O$_2$.C$_4$H$_4$O$_4$ | 108–109 | C 61.83 61.35 | H 6.24 6.21 | N 7.21 6.97 | |
| 61 | (3-phenyl-isothiazole, N-S) | —CH$_3$ | " | C$_{15}$H$_{18}$N$_2$OS.HCl | 166–167 | C 57.95 57.65 | H 6.17 6.13 | N 9.01 8.88 | Cl 11.40 11.67 |

TABLE 9-continued $$R^1-\overset{O}{\underset{\underset{R^2}{|}}{\overset{\|}{C}}}-CH-CH_2-N\overset{R^4}{\underset{R^5}{\diagdown}}$$

| Ex. | $R^1$ | $R^2$ | $-N\overset{R^4}{\underset{R^5}{\diagdown}}$ | Molecular formula | Melting point (°C.) | Elemental analysis data (%) Calcd (upper) Found (lower) | | | | |
|---|---|---|---|---|---|---|---|---|---|---|
| 62 | (benzisothiazole) | —CH₂CH₃ | " | C₁₆H₂₀N₂OS.HCl | 149–150 | C 60.60 60.09 | H 6.30 6.53 | N 8.32 8.40 | Cl 10.52 10.82 | |
| 63 | " | —CH₂CH₃ | —N(piperidine)-C(O)CH₃ | C₁₉H₂₄N₂SO₂.HCl | 163–164 | C 59.91 59.82 | H 6.61 6.54 | N 7.35 7.27 | Cl 9.31 9.27 | S 8.42 8.49 |
| 64 | (benzisothiazole) | —CH₂CH₃ | —N(morpholine)O | C₁₆H₂₀N₂O₂S.HCl | 151–152 | C 56.38 56.03 | H 6.21 6.16 | N 8.22 8.17 | Cl 10.40 10.35 | S 9.41 9.61 |
| 65 | Ph-isothiazole | —CH₃ | —N(pyrrolidine) | C₁₇H₂₀N₂SO.1.2HCl.0.5H₂O | 140–142 | C 57.81 57.53 | H 6.34 6.64 | N 7.93 8.44 | Cl 12.05 11.82 | |
| 66 | " | —CH₂CH₃ | " | C₁₈H₂₂N₂SO.HCl | 150–151 | C 61.61 61.80 | H 6.61 5.92 | N 7.99 8.00 | Cl 10.10 9.93 | S 9.14 9.41 |
| 67 | CH₃-isothiazole | —CH₃ | " | C₁₂H₁₈N₂OS.HCl | 157–159 | C 52.44 51.65 | H 6.98 6.90 | N 10.20 9.97 | Cl 12.90 12.88 | |
| 68 | Ph-isoxazole-CH₃ | —CH₃ | —N(piperidine) | C₁₉H₂₄N₂O₂.HCl | 161–162 | C 65.41 64.78 | H 7.22 7.30 | N 8.03 7.93 | Cl 10.16 9.90 | |

EXAMPLE 69

Centrally acting muscle relaxant effects and micturition reflex depression effects of certain aminoketone derivatives according to the present invention were confirmed by the following animal experiments.

1. Decerebrate rigidity remission action

Using the method proposed by Ono et al [H. Ono et al, Gen. Pharmacol., 18, 57 (1987)], rigidity remission action of the aminoketone derivatives of the invention for the decerebrate rigidity induced by radio frequency lesions of rat brains was investigated.

Procedure

Each Wistar male rat (body weight: 300–400 g) was anesthetized with ether and then fixed on a stereotaxic apparatus. In accordance with the Pellegrino's stereotaxic brain atlas, the electrodes of a lesion generator (manufactured by Radionics Company) were punctuated to AP: 0, L:±1.5, V:-3. While the electrodes were maintained at a tip temperature of 80° C., a high-frequency current of about 25 mA was applied for 180 seconds so that both left and right sites corresponding to brainstem cutting between the colliculus superior and the colliculus inferior were damaged. The rigidified rat was fixed in the abdominal position and one of the hind legs was pushed 4–5 mm toward the head repeatedy once a minute. The tension of each extension reflex of the extensor of the hind limbs was recorded. Assuming that the tension before the administration be 100%, the rate of rigidity inhibition as expressed in terms of percentage:

$$\left(100 - \frac{\text{Tension after administration}}{\text{Tension before administration}} \times 100\right)$$

The test compounds were intravenously administered at 3 mg/kg.

The results are summarized in Table 10.

TABLE 10

| Example No. | Rigidity inhibition, % |
|---|---|
| 1 | 40 |
| 5 | 40 |
| 8 | 38 |
| 20 | 49 |
| 21 | 44 |
| 22 | 41 |
| 28 | 62 |

TABLE 10-continued

| Example No. | Rigidity inhibition, % |
|---|---|
| 29 | 53 |
| 34 | 60 |
| 46 | 51 |
| 52 | 61 |
| Eperisone hydrochloride | 52 |

2. Depressing Action for the Spinal Reflex of Cat

Procedure

Both male and female cats having a body weight of 2.5–4.0 kg were anesthetized with ether and then fixed in the supine position. In accordance with the method proposed by Shimamoto et al ["Yakurigaku Jisshu (Pharmacological Practice)", Nanzando Co., Ltd. (1960)], profound peroneal nerve-anterior peroneal nerve samples were prepared for the testing of flexor reflex. The flexor reflex of the right anterior tibialis was elicited by electrical stimulation (0.2 Hz, 1 ms, supra maximal voltage) of the central end of the ipsilateral femoral nerve. Under a static tension of 25 g, contractions of the corresponding anterior peroneal nerve were recorded on a polygraph. Assuming that the contraction force before the administration be 100%, the rate of flexor reflex inhibition was expressed in terms of percentage:

$$\left(100 - \frac{\text{Contraction force after administration}}{\text{Contraction force before administration}} \times 100\right)$$

The test compounds were intravenously administered at 3 mg/kg.

The results are summarized in Table 11.

TABLE 11

| Example No. | Reflex inhibition, % |
|---|---|
| 20 | 54 |
| 28 | 79 |
| 29 | 70 |
| 38 | 38 |
| 46 | 66 |
| 47 | 45 |
| 58 | 45 |
| 61 | 85 |
| 62 | 90 |
| 68 | 56 |
| Eperisone hydrochloride | 50 |

3. Antiepileptic Action ddy Male mice (body weights: 25–30 g) were used. Test compounds were intraperitoneally administered. Thirty minutes later, pentetrazole (PTZ) was intraperitoneally administered at 170 mg/kg.

Tonic extension of the hind limbs was observed. Antiepileptic action (%)

$$\text{Antiepileptic action (\%)} = \frac{\text{Number of mice not developed tonic extension}}{\text{Number of mice tested}} \times 100$$

Effective dose for 50% of antiepileptic action, $ED_{50}$ (mg/kg) was calculated. The results are summarized in Table 12.

TABLE 12

| Example No. | Antiepileptic action $ED_{50}$ (mg/Kg) |
|---|---|
| 1 | 17 |
| 5 | 20 |
| 22 | 18 |
| 28 | 5 |
| 29 | 3 |
| 61 | 11 |
| 62 | 23 |
| 68 | 17 |
| Eperisone hydrochloride | 30 |

4. Micturition Reflex Depression Action

Wistar male rats having a body weight of 300 g were each anesthetized s.c. with 1.5 g/kg of urethane and fixed in the supine position. The hypogastrium was next subjected to median incision so that the bladder was exposed. A short cut was formed in a top part of the bladder, through which a balloon having an internal volume of about 1 ml was inserted. A catheter equipped with a three-way cock was connected to the balloon. A syringe was connected to another flow passage of the three-way cock, while a transducer ("Statham P-50", trade name) was connected to the remaining flow passage to permit the measurement of the internal pressure of the bladder.

After the rat was left over for at least 30 minutes after the operation, 0.25–0.5 ml of distilled water was injected into the balloon by means of the syringe. Variations in the internal pressure of the bladder, which were developed at that time due to spontaneous movement of the bladder, were recorded on a polygraph ("RM-6000", trade name; manufactured by Nihon Koden K.K.) by way of the transducer.

Each test compound was dissolved in physiological saline and injected through the common carotid vein. Effects of each test compound was expressed in terms of the time required until the disappearance of a contraction of the bladder caused by a micturition reflex.

As are shown in Table 13, the test compounds exhibited stronger micturition reflex depressing action than the control compound, i.e., eperisone.

TABLE 13

| | Micturition Reflex Depressing Action | | |
|---|---|---|---|
| Example No. | Dose (mg/kg) | Number of rats tested | Time required until disappearance (min) |
| Control | — | 3 | 0.3 ± 0.1 |
| 28 | 2 | 3 | 5.6 ± 1.2* |
|  | 4 | 3 | 10.1 ± 2.1** |
| 29 | 2 | 3 | 4.9 ± 1.2* |
|  | 4 | 3 | 8.6 ± 2.1** |
| Eperisone hydro-chloride | 2 | 3 | 2.4 ± 1.2 |
|  | 4 | 3 | 5.8 ± 2.1* |

Mean ± S.E.
*$p < 0.05$
**$p < 0.01$

5. Central Depressant Action

Depressant action against spontaneous behavior using a revolutionary wheel was used as an index for central depressant action.

ddy Male mice (body weights: 25–30 g) were used. After intraperitoneal administration of each test compound, the mouse was immediately placed in a revolutionary wheel. The total number of revolutions of the wheel during a 20 minute period immediately after the placement of the mouse inside the wheel was counted.

Doses required to reduce the number of revolutions by 50%, $ED_{50}$ (mg/kg) were determined.

The results are shown in Table 14.

TABLE 14

| Example No. | Central depressant action $ED_{50}$ (mg/Kg) |
| --- | --- |
| 1 | 54 |
| 5 | 44 |
| 20 | 49 |
| 21 | 52 |
| 22 | 43 |
| 28 | 44 |
| 29 | 38 |
| 61 | 37 |
| 62 | 50 |
| Eperisone hydrochloride | 33 |

4. Acute Toxicity ddy Male mice (body weights: 25-30 g) were used. Each test compound was intraperitoneally administered. One day later, the mice were observed whether they were alive or dead.

50% lethal doses, $LD_{50}$ (mg/kg) were calculated.

The results are summarized in Table 15.

TABLE 15

| Example No. | $LD_{50}$ (mg/kg) |
| --- | --- |
| 1 | 170-300 |
| 5 | 100-170 |
| 20 | 170-300 |
| 28 | 100-170 |
| 29 | 300-500 |
| Eperisone hydrochloride | 100-170 |

REFERENCE EXAMPLE 1

3-phenyl-5-butyrylisoxazole 10 g ( 0.082) of benzaldoxime and 9 g ( 0.092 mol) of 1-hexine-3-ol were dissolved in 50 ml of dichloromethane. The resultant reaction solution was ice-cooled, and 58 g (0.1 mol) of a 12% aqueous sodium hypochlorite solution were added dropwise to the solution, while a solution temperature was maintained at 15° to 25° C. After the addition, the solution was stirred for 3 hours, while the solution temperature was maintained at 15 to 25° C.

49 g (0.079 mol) of the 12% aqueous sodium hypochlorite solution were added dropwise to the reaction solution. The temperature of the reaction solution was cooled to 10° C., and an aqueous pyridine hydrochloride solution (which was prepared from 2.8 ml of 6 N hydrochloric acid and 1.3 ml of pyridine) was added dropwise thereto over 20 minutes. The reaction solution was stirred for 70 minutes, and 49 g (0.079 mol) of the 12% aqueous sodium hypochlorite solution were then added dropwise thereto.

The temperature of the solution was cooled to 10° C., and an aqueous pyridine hydrochloride solution (which was prepared from 1.4 ml of 6 N hydrochloric acid and 0.67 ml of pyridine) was added dropwise thereto over 10 minutes, followed by stirring for 70 minutes. 49 g (0,079 mol) of the 12% aqueous sodium hypochlorite solution were then added dropwise to this solution. The temperature of the solution was cooled to 10° C. again, and the aqueous pyridine hydrochloride solution and the 12% aqueous sodium hypochlorite solution were similarly added.

100 ml of a 5% aqueous sodium hydrogensulfite solution were added to a dichloromethane layer obtained by separating the reaction solution, followed by stirring for 30 minutes. The dichloromethane layer obtained by separating the reaction solution was washed with 100 ml of water and 100 ml of a 1 N aqueous hydrochloric acid solution in this order. The washed dichloromethane layer was heated and concentrated to obtain a residue, and this residue was then recrystallized from 40 ml of ethanol, thereby obtaining 10.6 g (yield 59.6% ) of the desired compound. Melting point 89°-90° C.

REFERENCE EXAMPLE 2

[3-phenyl-5-[2- ( 1 -pyrrolidinylmethyl)butyryl]-isoxazole hydrochloride ]

20 g (93 mmol) of 3-phenyl-5-butyrylisoxazole and 7.93 g (111 mmol) of pyrrolidine were added to 62 g of methanol. To the solution, 9.04 g (111 mmol) of a 37% aqueous formalin solution were added dropwise, while the solution temperature was maintained at 20° to 30° C. After completion of the addition, the solution was stirred for 1 hour, while the solution temperature was maintained at 20° to 30° C.

178 g of ethyl acetate were added to the resultant reaction solution. 150 g of water were further added thereto, and separation and extraction were then carried out to obtain an organic layer. The obtained organic layer was ice-cooled, and 178 g of a 2 N aqueous hydrochloric acid solution were added, followed by separation and extraction. The resultant aqueous layer was extracted with 180 g of chloroform. The aqueous layer was extracted with 120 g of chloroform again, and the resultant chloroform layers were joined and dried over anhydrous sodium sulfate. This sodium sulfate was removed by filtration to obtain a chloroform solution, and 294 g of ethyl acetate were added dropwise to the chloroform solution with stirring. The solution was ice-cooled to precipitate crystals, and these crystals were then collected by filtration, washed with ethyl acetate, and then dried under reduced pressure to obtain 20.8 g (yield 67%) of the desired colorless compound. Melting point 151°-153° C.

REFERENCE EXAMPLE 3

[3-phenyl-5-[2-(1-pyrrolidinylmethyl)butyryl]-isoxazole]

125 g (0.37 mol) of 3-phenyl-5-[2-(1-pyrrolidinylmethyl)butyryl]isoxazole hydrochloride were added to a mixture of 400 ml of water and 300 ml of ethyl acetate. 620 ml of a 6% aqueous sodium hydrogencarbonate solution were further added dropwise to the solution under ice-cooling to precipitate crystals.

100 ml of ethyl acetate were added to this solution to dissolve the precipitated crystals, followed by separation, thereby obtaining an ethyl acetate layer. The aqueous layer was extracted with 500 ml of ethyl acetate again to obtain an ethyl acetate layer. These organic layers were joined, and then washed with 250 ml of water and 250 ml of a saturated sodium chloride solution. The ethyl acetate solution was dried with anhydrous sodium sulfate, and sodium sulfate was removed by filtration. The resultant filtrate was concentrated to dryness under reduced pressure, thereby obtaining 110 g (yield 98.9%) of the desired compound. Melting point 68°–69° C.

EXAMPLE 70

[(+)-3-phenyl-5-[2-(1-pyrrolidinylmethyl)butyryl]-isoxazole hydrochloride]

(1) (+)-3-phenyl-5-[2-(1-pyrrolidinylmethyl)-butyryl]isoxazole L-10-camphorsulfonate 10 g (0.03 mol) of 3-phenyl-5-[2-(1-pyrrolidinylmethyl)butyryl]isoxazole hydrochloride were dissolved in a mixture of 60 ml of water and 70 ml of ethyl acetate. 72 ml of a 6% aqueous sodium hydrogencarbonate solution were added dropwise to the solution. The reaction solution was stirred for 10 minutes, followed by separation to obtain an organic layer. The aqueous layer was extracted with 60 ml of ethyl acetate again, and the resultant organic layer was joined with the previously obtained organic layer, and the solution was then dried over anhydrous sodium sulfate. This sodium sulfate was then removed by filtration, and 14.2 g (0.06 mol) of L-10-camphorsulfonic acid {$[\alpha]^{20}_D=21°$ (c=2, water)} were added to the resultant filtrate, and they were stirred for 30 minutes to dissolve the same. The reaction solution was stirred for 6 hours under ice-cooling to precipitate crystals, and the crystals were collected by filtration, washed with ethyl acetate, and then dried under reduced pressure, thereby obtaining the desired (+)-3-phenyl-5-[2-(1-pyrrolidinylmethyl)butyryl]isoxazole L-camphor-sulfonate. Yield (weight) 9.5 g Yield (ratio) 42% Melting point 115.8°–116.3° C. $[\alpha]^{20}_D=-14.4°$ (c=0.5, ethanol) Optical purity 98.7% ee (2) (+)-3-phenyl-5-[2-(1-pyrrolidinylmethyl)-butyryl]isoxazole hydrochloride 9.4 g (12.3 mol) of (+)-3-phenyl-5-[2-(1-pyrrolidinylmethyl)butyryl]isoxazole L-10-camphorsulfonate were dissolved in a mixture of 54 ml of water and 54 ml of ethyl acetate. 30 ml of a 10% aqueous sodium carbonate solution were added dropwise to the solution. The reaction solution was stirred for 10 minutes, followed by separation to obtain an organic layer. The thus obtained organic layer was washed with 15 ml of a 10% aqueous sodium carbonate solution and 15 ml of water. 28 ml of a 2 N aqueous hydrochloric acid solution were added to this organic layer, followed by separation and extraction to obtain an aqueous layer. The organic layer was extracted with 15 ml of the 2 N aqueous hydrochloric acid solution again to obtain an aqueous layer, and this aqueous layer was joined with the previously obtained aqueous layer. 17.6 ml of chloroform were added to the joined aqueous solution, followed by extraction to obtain a chloroform layer. The aqueous layer was extracted with 17.6 ml of chloroform again, and the resultant chloroform layer was joined with the previously obtained chloroform layer. The thus obtained chloroform solution was then dried over anhydrous sodium sulfate. This sodium sulfate was then removed by filtration, 106 ml of ethyl acetate were added dropwise to the chloroform solution. This solution was stirred for 3 hours under ice-cooling. The precipitated crystals were collected by filtration, and then washed with ethyl acetate, thereby obtaining the desired (+)-3-phenyl-5-[2-(1-pyrrolidinylmethyl)butyryl]isoxazole hydrochloride. Yield (weight) 3.4 g Yield ( ratio ) 82% Melting point 158°–159.5° C. $[\alpha]^{20}_D=+29°$ (c=0.5, water) Optical purity 99.9% ee or more NMR (CDCl$_3$, $\delta_{ppm}$); 0.99 (3H, t, J=7.3 Hz), 1.77–1.83 (1H, m), 1.88–1.97 (1H, m), 1.98–2.11 (2H, m), 2.11–2.23 (2H, m), 2.70–2.78 (1H, m), 2.79–2.95 (1H, m), 3.33 (1H, m), 3.47–3.64 (1H, m), 3.68–3.71 (1H, m), 3.83–3.87 (1H, m), 4.33–4.38 (1H, m), 7.48–7.50 (3H, m), 7.76 (1H, s), 7.87–7.90 (2H, m)

Elemental Analysis (C$_{18}$H$_{22}$N$_2$O$_2$.HCl): Calcd. C:64.57, H:6.92, N:8.37, Cl:10.59; Found C:64.51, H:6.96, N:8.20, Cl:10.42.

EXAMPLE 71

[(−)-3-phenyl-5-[2-(1-pyrrolidinylmethyl)butyryl]-isoxazole hydrochloride]

(1) (−)-3-phenyl-5-[2-(1-pyrrolidinylmethyl)-butyryl]isoxazole D-10-camphorsulfonate 10 g (33.3 mmol) of 3-phenyl-5-[2-(1-pyrrolidinylmethyl)butyryl]isoxazole were dissolved in 200 ml of ethyl acetate. 11.5 g (67 mmol) of D-10-camphorsulfonic acid {$[\alpha]^{20}_D=+19.9°$ (c=2, water)} were added to the resultant solution, followed by stirring for 30 minutes to dissolve the same. The solution was stirred for 2 hours under ice-cooling to precipitate crystals, and the crystals were collected by filtration, washed with ethyl acetate, and then dried under reduced pressure, thereby obtaining the desired (−)-3-phenyl-5-[2-(1-pyrrolidinylmethyl)butyryl]-isoxazole D-camphorsulfonate. Yield (weight) 11.8 g Yield (ratio) 46% Melting point 120°–121° C. $[\alpha]^{20}_D=+17°$ (c=0.5, ethanol) Optical purity 96% ee (2) (−)-3-phenyl-5-[2-(1-pyrrolidinylmethyl)-butyryl]isoxazole hydrochloride 7.0 g (9.2 mmol) of (−)-3-phenyl-5-[2-(1-pyrrolidinylmethyl)butyryl]isoxazole D-10-camphorsulfonate were dissolved in a mixture of 40 ml of water and 40 ml of ethyl acetate. 22 ml of a 10% aqueous sodium carbonate solution were added thereto, followed by stirring for 10 minutes. The reaction solution was separated to obtain an organic layer. The thus obtained organic layer was washed with 11 ml of a 10% aqueous sodium carbonate solution. The organic layer was extracted with 17 ml of a 2 N aqueous hydrochloric acid solution twice and the resultant aqueous layers were then joined. This aqueous solution was extracted twice with 12 ml of chloroform and the chloroform layers were joined. The thus obtained chloroform solution was then dried over anhydrous sodium sulfate. This sodium sulfate was then removed by filtration, and 72 ml of ethyl acetate were added dropwise to the chloroform solution. The solution was then stirred at room temperature for 1 hour and further stirred for 1 hour under ice-cooling. The precipitated crystals were collected by filtration, thereby obtaining the desired (−)-3-phenyl-5-[2-(1-pyrrolidinylmethyl)butyryl]isoxazole hydrochloride. Yield (weight) 2.5 g Yield (ratio) 81% Melting point 145°–146° C. $[\alpha]^{20}_D=-27°$ (c=0.5, water) Optical purity 99.85% or more NMR (CDCl$_3$, $\delta_{PPM}$); 0.99 (3H, t, J=7.3 Hz), 1.77–1.82 (1H, m), 1.88–1.98 (1H, m), 2.06–2.14 (2H, m), 2.14–2.24 (2H, m), 2.71–2.73 (1H, m), 2.81–2.88 (1H, m), 3.32 (1H, bd), 3.47 (1H, bs), 3.61–3.64 (1H, m), 3.66–3.69 (1H, m), 4.34–4.40 (1H, m), 7.48–7.52 (3H, m), 7.75 (1H, s), 7.89–7.91 (2H, m)

Elemental Analysis (C$_{18}$H$_{22}$N$_2$O$_2$.HCl): Calcd. C:64.57, H:6.92, N:8.37, Cl:10.59; Found C:64.65, H:6.79, N:8.03, Cl:10.81.

EXAMPLE 72

[(+)-3-phenyl-5-[2-(1-pyrrolidinylmethyl)butyryl]-isoxazole hydrochloride]

54 ml of water were added to a filtrate obtained when (−)-3-phenyl-5-[2-(1-pyrrolidinylmethyl)butyryl]-isoxazole D-10-camphorsulfonate was collected by filtration in Example 71 (1), and 45 ml of a 10% aqueous sodium carbonate solution were added dropwise thereto. After stirred for 10 minutes, the reaction solution was separated to obtain an organic layer. The obtained organic layer was washed with 20 ml of a 10% aqueous sodium carbonate solution, and further washed with 20 ml of water. 40 ml of a 2 N aqueous hydrochloric acid solution were added to the organic layer, followed by separation and extraction to obtain an aqueous layer. The organic layer was extracted with 30 ml of the 2 N aqueous hydrochloric acid solution again to obtain an aqueous layer, and this aqueous layer was then joined with the previously obtained aqueous layer. 40 ml of chloroform were added to the aqueous solution, followed by extraction to obtain a chloroform layer. 40 ml of chloroform were added to the aqueous layer and the solution was then extracted to obtain a chloroform layer, which was joined with the previously obtained chloroform layer. The thus obtained chloroform solution was dried over anhydrous sodium sulfate. This sodium sulfate was removed by filtration, and 240 ml of ethyl acetate were then added dropwise to the chloroform solution. This solution was stirred for 3 hours under ice-cooling. The precipitated crystals were collected by filtration and then washed with ethyl acetate to obtain 4.5 g (optical purity 87% ee) of the desired (+)-3-phenyl-5-[2-(1-pyrrolidinylmethyl)butyryl]isoxazole hydrochloride. 4.5 g of this hydrochloride were dissolved in 40 ml of chloroform. 120 ml of ethyl acetate were added dropwise to this solution, followed by stirring for 3 hours under ice-cooling. The precipitated crystals were collected by filtration, thereby obtaining the desired (+)-3-phenyl-5-[2-(1-pyrrolidinylmethyl)butyryl]isoxazole hydrochloride. Yield (weight) 3.6 g Yield (ratio) 59% Melting point 158°–159° C. [α]$^{20}_D$ = +28° (c=0.5, water) Optical purity 99.5% ee

EVALUATION EXAMPLE

A centrally acting muscle relaxant action, an action to skeletal muscle afferent discharge and acute toxicity of an optically active aminoketone derivative of the present invention were confirmed by the following animal experiments.

1. Decerebrate rigidity remission action

Using the method suggested by Ono et al- [H. Ono et al., Gen. Pharmacol., 18, 57 (1987)], the rigidity remission action of the optically active aminoketone derivative of the present invention for the decerebrate rigidity induced by radio frequency lesions of rat brains was investigated.

Procedure

Each Wistar male rat (body weight: 300–400 g) was anesthetized with ether and then fixed on a stereotaxic apparatus. In accordance with the Pellegrino's stereotaxic brain atlas, the electrodes of a lesion generator (manufactured by Radionics Company) were punctuated to AP: O, L: ±1.5, V: −3. While the electrodes were maintained at a tip temperature of 80° C., a high-frequency current of about 25 mA was applied for 180 seconds so that both left and right sites corresponding to brainstem cutting between the colliculus superior and the colliculus inferior were damaged. The rigidified rat was fixed in the abdominal position, and the tension of each extension reflex of the extensor of the hind limbs was recorded. Assuming that the tension before the administration was 100%, the rate of rigidity inhibition is expressed in terms of percentage:

$$\left(100 - \frac{\text{Tension after administration}}{\text{Tension before administration}} \times 100\right)$$

The test compounds were intravenously administered at 3 and 6 mg/kg. The results are set forth in Table 16.

TABLE 16

| | Test Compound | Dose (mg/kg, i.v.) | Rigidity Inhibition (%) |
|---|---|---|---|
| 1. | (+) form | 3 | 59 |
| | | 6 | 78 |
| 2. | (−) form | 3 | 33 |
| | | 6 | 53 |
| 3. | racemic form | 3 | 56 |
| | | 6 | 65 |

2. Action to skeletal muscle afferent discharge

The musculus triceps surae was separated from each of Wistar rats (9 to 10 weeks old; Japanese rats) under a mixed anesthetic of urethane and α-chlorarose. There were cut out all the branches of the sciatic nerve except the branch which controls the musculus triceps surae. The medulla spinalis was subjected to laminectomy, and roots of L6 or less were cut out. Next, L4 and L5 posterior roots on the same side were cut and separated from the central end, and L4 and L5 anterior roots were cut out for the purpose of eliminating the influence of the superior central. A nerve fiber coming from the musculus triceps surae was only separated from the L5 posterior root. A tension of 20 g was applied to the peripheral end of the musculus riceps surae, and each discharge frequency of the nerve was recorded. Assuming that the discharge frequency before the administrationis 100%, the discharge frequency of the nerve was expressed in terms of percentage:

$$\left(100 - \frac{\text{Discharge frequency at most inhibition}}{\text{Discharge frequency before administration}} \times 100\right)$$

The test compounds were intravenously administered at 6 to 12 mg/kg. The results are set forth in Table 17.

TABLE 17

| | Test Compound | Dose (mg/kg, i.v.) | Discharge Frequency (%) |
|---|---|---|---|
| 1. | (+) form | 6 | 28 |
| | | 12 | 14 |
| 2. | (−) form | 6 | 83 |
| 3. | racemic form | 6 | 46 |
| | | 12 | 27 |

2. Acute Toxicity ddy Male mice (body weights: 25–30 g) were used. Each test compound was intraperitoneally administered, and 72 hours later, the mice were observed as to whether they were alive or dead.

50% lethal doses $LD_{50}$ (mg/kg) were calculated. The results are set forth in Table 18.

TABLE 18

| Test Compound | $LD_{50}$ (mg/kg) |
|---|---|
| 1. (+) form | 386 |
| 2. (−) form | 760 |
| 3. racemic form | 445 |

According to the centrally acting muscle relaxant action (Table 16) represented by the decerebrate rigidity remission action, it is apparent that the (+) form is much more excellent as compared with the racemic form and the (−) form. Furthermore, the function for inhibiting the skeletal muscle afferent discharge is very effective to relax the abnormal tension of the muscle spindle. The (+) form is more excellent in the function for inhibiting the skeletal muscle afferent discharge (Table 17) as compared with the racemic form and the (−) form. With regard to the acute toxicity, the (+) form is substantially equal to the racemic form. In consequence, it is fair to say that (+)-3-phenyl-5-[2-(1-pyrrolidinylmethyl)-butyryl]isoxazole is a very excellent centrally acting muscle relaxant.

What is claimed is:

1. An aminoketone derivative represented by the following formula (I):

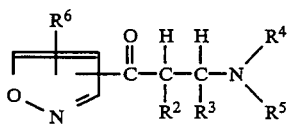

(I)

wherein $R^6$ represents a phenyl group optionally substituted by one or more substituents selected from the group consisting of halogen atoms, lower alkoxy groups, lower alkyl groups, trifluoromethyl groups, cyano groups, nitro groups, amino groups, dimethylamino groups, acetamido groups, methanesulfonylamido groups, acetyl groups and lower alkoxycarbonyl groups;

$R^2$ represents a hydrogen atom, a lower alkyl, benzyl, methoxy, phenyl, allyl trifluoromethyl- or lower-alkoxy-substituted lower alkyl, or cyclopropylmethyl group;

$R^3$ represents a hydrogen atom or a lower alkyl alkyl group excluding that $R^2$ and $R^3$ are both hydrogen atoms, or $R^2$ and $R^3$ are coupled together to form a five- or six-membered alicylic group; and $R^4$ and $R^5$ are coupled together into a cyclic form to from at least one cyclic structure selected from the group consisting of a pyrrolidino group, a piperidino group and a hexamethyleneimino group, said cyclic structure being optionally substituted by one or more substituents selected from the group consisting of methyl, acetyl and benzyl groups.

2. A physiologically acceptable salt of the aminoketone derivative according to claim 1.

3. An aminoketone derivative represented by the following formula (I), or a physiologically acceptable salt thereof:

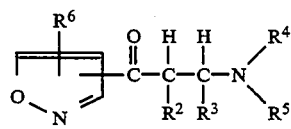

(I)

wherein $R^6$ represents a phenyl group optionally substituted by one or more substituents selected from the group consisting of halogen atoms, $C_{1-2}$ alkoxy groups, $C_{1-2}$ groups, trifluoromethyl groups, cyano groups, nitro groups, amino groups, dimethylamino groups, acetamido groups, methaneszulfonylamido groups, acetyl groups and $C_{1-2}$ alkoxycarbonyl groups;

$R^2$ represents a hydrogen atom, a $C_{1-4}$ alkyl, benzyl, methoxy, phenyl, allyl, trifluoromethyl- or $C_{1-2}$-alkoxy-substituted $C_{1-2}$ alkyl, or cyclopropylmethyl group;

$R^3$ represents a hydrogen atom or a $C_{1-2}$ alkyl group, or $R^2$ and $R^3$ are coupled together to form a five- or six-membered alicyclic group provided $R^2$ and $R^3$ are not both hydrogen; and $R^4$ and $R^5$ are coupled together into a cyclic form to form a pyrrolidino group optionally substituted by one or more substituents selected from the group consisting of methyl, acetyl and benzyl groups.

4. 3-phenyl-5-[2-(1-pyrrolidinylmethyl)-butyryl] isoxazole represented by the formula (1)

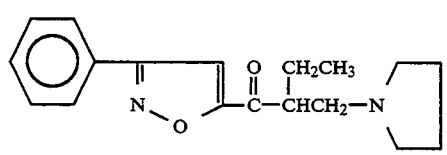

(1)

and its salt physiologically acceptable.

5. (+)3-phenyl-5-[2-(1-pyrrolidinylmethyl)butyryl]isoxazole represented by the formula (2)

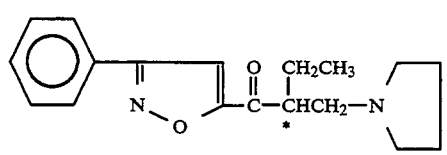

(2)

physiologically acceptable and its salt

6. A centrally acting muscle relaxant composition comprising as an active ingredient the aminoketone derivative of claim 1 or 3 or a physiologically acceptable salt thereof together with a pharmaceutically acceptable carrier or diluent.

7. A method of achieving centrally acting muscle relaxation in a person comprising administering to a person in need of same an effective amount of an aminoketone derivatives of claim 1 or 3 or a physiologically acceptable salt thereof.

* * * * *